(12) United States Patent
Smyth et al.

(10) Patent No.: US 12,151,062 B2
(45) Date of Patent: Nov. 26, 2024

(54) COMPOSITIONS AND DEVICES TO ADMINISTER PHARMACEUTICAL COMPOSITIONS NASALLY

(71) Applicant: BOARD OF REGENTS, THE UNIVERSITY OF TEXAS SYSTEM, Austin, TX (US)

(72) Inventors: Hugh D. C. Smyth, West Lake Hills, TX (US); Robert O. Williams, III, Austin, TX (US); Zachary Warnken, Austin, TX (US); Yang Lu, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 18/327,723

(22) Filed: Jun. 1, 2023

(65) Prior Publication Data

US 2023/0381434 A1 Nov. 30, 2023

Related U.S. Application Data

(62) Division of application No. 16/339,922, filed as application No. PCT/US2017/054861 on Oct. 3, 2017, now abandoned.

(Continued)

(51) Int. Cl.
*A61M 15/08* (2006.01)
*A61K 9/00* (2006.01)
(Continued)

(52) U.S. Cl.
CPC .......... *A61M 15/08* (2013.01); *A61K 9/0043* (2013.01); *A61K 9/0085* (2013.01); *A61K 9/122* (2013.01);
(Continued)

(58) Field of Classification Search
CPC ............... A61M 15/08; A61M 31/005; A61M 2025/0226; A61M 2202/064; A61M 2205/3327; A61M 2210/0618; A61M 2205/3306; A61M 11/02; A61K 9/0043; A61K 9/0085; A61K 9/122; A61K 9/124;
(Continued)

(56) References Cited

U.S. PATENT DOCUMENTS

| 7,231,919 B2 | 6/2007 | Giroux et al. |
| 2004/0176719 A1* | 9/2004 | Ishizeki ............... A61M 15/08 604/275 |

(Continued)

OTHER PUBLICATIONS

International Search Report and Written Opinion of International Application No. PCT/US2017/054861, mailed Feb. 2, 2018.
(Continued)

*Primary Examiner* — Van D Huynh
(74) *Attorney, Agent, or Firm* — Parker Highlander PLLC

(57) ABSTRACT

Devices and methods for nasal administration of a pharmaceutical composition. In certain embodiments, the devices comprises a reservoir, a conduit in fluid communication with the reservoir, and an anatomic positioning device configured to position the conduit in a nasal cavity of a user. Particular embodiments include an actuator configured to transfer the pharmaceutical composition from the reservoir to the conduit and emit the pharmaceutical composition from the conduit.

6 Claims, 18 Drawing Sheets

Related U.S. Application Data

(60) Provisional application No. 62/404,928, filed on Oct. 6, 2016.

(51) Int. Cl.

| | | |
|---|---|---|
| *A61K 9/12* | (2006.01) | |
| *A61K 9/14* | (2006.01) | |
| *A61K 31/4184* | (2006.01) | |
| *A61K 47/32* | (2006.01) | |
| *A61K 49/00* | (2006.01) | |
| *A61K 49/06* | (2006.01) | |
| *A61M 31/00* | (2006.01) | |
| *G16H 20/10* | (2018.01) | |
| *G16H 40/63* | (2018.01) | |
| *A61B 5/055* | (2006.01) | |
| *A61B 6/03* | (2006.01) | |
| *A61M 25/02* | (2006.01) | |

(52) U.S. Cl.
CPC ............. *A61K 9/124* (2013.01); *A61K 9/146* (2013.01); *A61K 31/4184* (2013.01); *A61K 47/32* (2013.01); *A61K 49/0043* (2013.01); *A61K 49/06* (2013.01); *A61M 31/005* (2013.01); *G16H 20/10* (2018.01); *G16H 40/63* (2018.01); *A61B 5/055* (2013.01); *A61B 6/032* (2013.01); *A61M 2025/0226* (2013.01); *A61M 2202/064* (2013.01); *A61M 2205/3327* (2013.01); *A61M 2210/0618* (2013.01)

(58) Field of Classification Search
CPC .... A61K 9/146; A61K 31/4184; A61K 47/32; A61K 49/0043; A61K 49/06; G16H 20/10; G16H 40/63; A61B 5/055; A61B 6/032
USPC ......................................................... 600/432
See application file for complete search history.

(56) References Cited

U.S. PATENT DOCUMENTS

| | | | | |
|---|---|---|---|---|
| 2007/0119451 | A1* | 5/2007 | Wang .................... | A61M 15/08 128/207.18 |
| 2008/0015544 | A1* | 1/2008 | Keith .................... | A61B 17/24 604/516 |
| 2009/0314293 | A1* | 12/2009 | Djupesland ........... | A61M 15/08 128/203.18 |
| 2010/0329984 | A1* | 12/2010 | Weers .................. | A61K 9/0075 424/9.1 |
| 2011/0015734 | A1* | 1/2011 | Gonzales ............... | A61B 17/24 606/199 |
| 2014/0311482 | A1* | 10/2014 | Levitt, Jr. .............. | A61P 27/14 128/200.14 |
| 2016/0128863 | A1* | 5/2016 | Loomas ............. | A61M 15/002 128/848 |

OTHER PUBLICATIONS

International Preliminary Report on Patentability of International Application No. PCT/US2017/054861, mailed May 16, 2019.

* cited by examiner

FIGS. 1A-C

| Angle A | Angle B | Deposition Percent in Upper Region |
|---------|---------|-----------------------------------|
| 0 | 0 | 13.4% |
| 0 | 30 | 9.3% |
| 15 | 15 | 10.5% |
| 20 | 0 | 12.1% |
| 7* | 23* | 22.8% |

[*] Optimal angle found for the individualized 3D-printed nasal cast

| Fraction | Amount |
|---|---|
| 2.5% Poloxamer 407;0.1% HPMC E4M aq. Solution | 11.27 g |
| Perfluorooctylbromide (PFOB) | 0.75 g |
| Fluorescein | 15 mg |
| 3% NaOH solution | 100 µL |
| HFA 227 | 2.5 g |

| | Anterior | Upper | Middle | Lower | Nasopharynx |
|---|---|---|---|---|---|
| Percent Deposited | 9.0 | 27.9 | 29.5 | 33.6 | 0 |

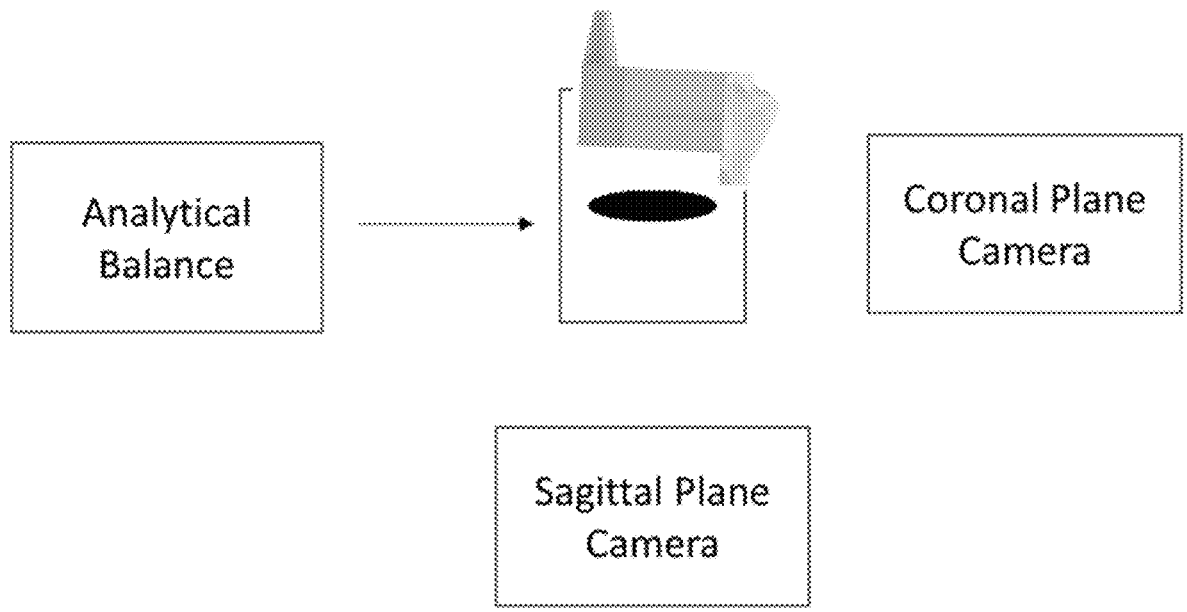
FIG. 21
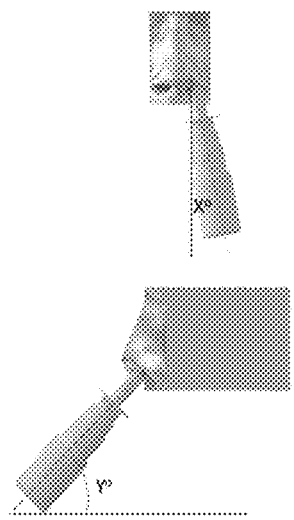
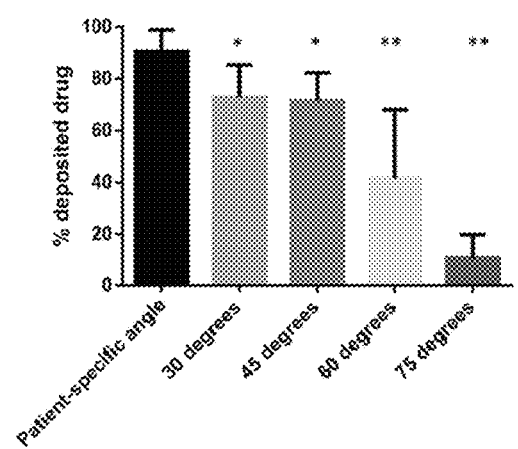
FIG. 22

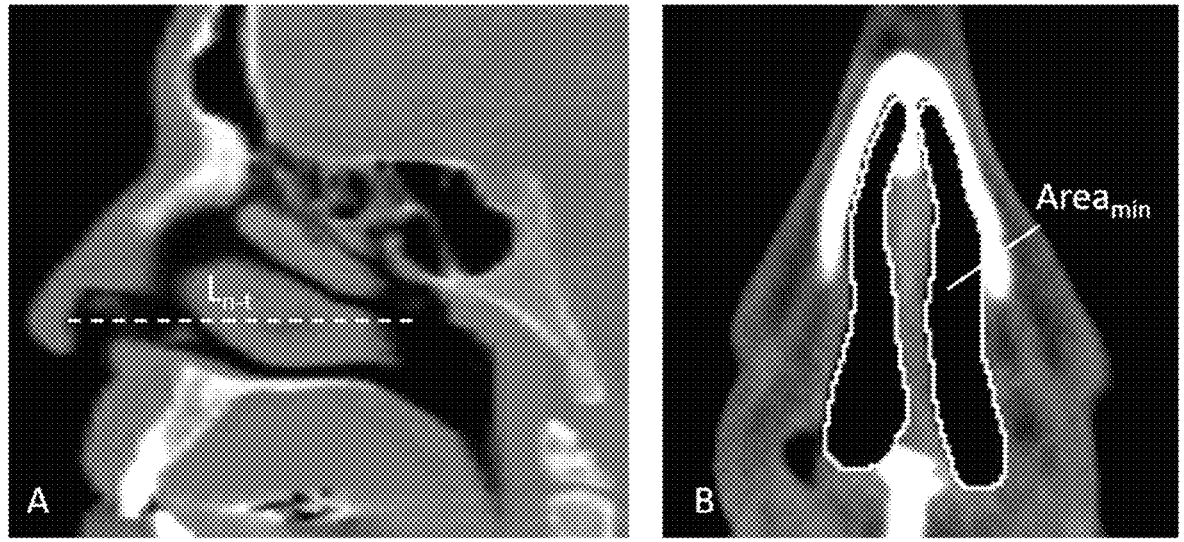
FIGS. 23A-B
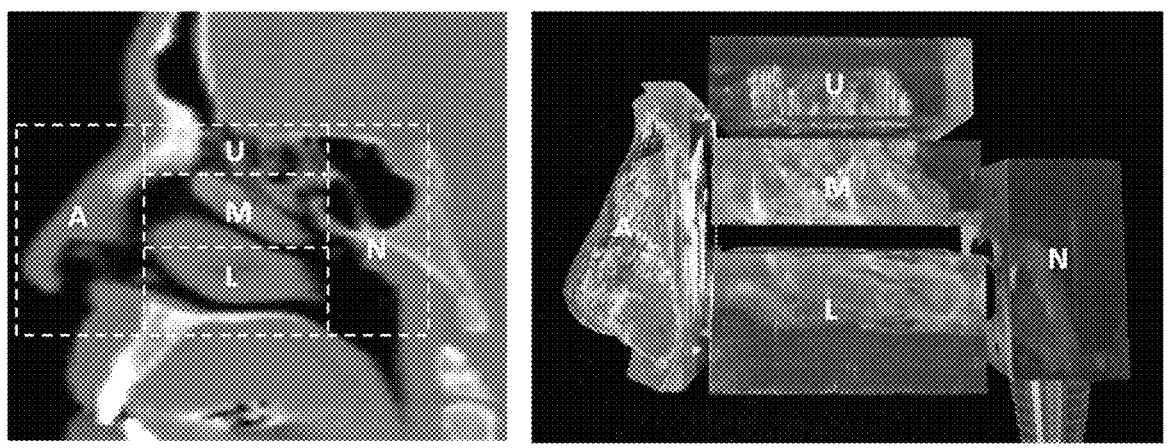
FIG. 24

COMPOSITIONS AND DEVICES TO ADMINISTER PHARMACEUTICAL COMPOSITIONS NASALLY

This application is a divisional of U.S. patent application Ser. No. 16/339,922, filed Apr. 5, 2019, as a national phase application under 35 U.S.C. § 371 of International Application No. PCT/US2017/054861, filed Oct. 3, 2017, which claims the benefit of U.S. Provisional Patent Application No. 62/404,928, filed Oct. 6, 2016, the entirety of each which is incorporated herein by reference.

BACKGROUND INFORMATION

Currently, oral administration is the most common method of drug delivery, and is most often used for absorption into the systemic circulation.[1] However, when the disease in question is a CNS related disorder, there are several additional barriers that a drug must overcome to reach its site of action and provide a pharmacological response such as the blood-brain barrier (BBB) and the blood-cerebrospinal fluid barrier.[2] Over the last several decades, it has been discovered that materials can be transported directly to the brain interstitial fluid and cerebrospinal fluid when administered intranasally.[3,4] By using intranasal administration, it is possible to circumvent the barriers of the BBB by taking advantage of the only place the CNS is in direct contact with the environment, the olfactory epithelium.[4] In the past, invasive methods such as intraparenchymal, intrathecal, and intracerebroventricular injections have been used to achieve clinically relevant brain concentrations for therapeutic efficacy. Limitations of nose-to-brain delivery have also been identified, and include a relatively small volume for administration of the drug, limited surface area of the olfactory epithelium and short retention time for drug absorption.[5]

Accordingly, several studies have attempted different formulation techniques to improve brain delivery by direct nose-to-brain mechanisms. Studies have shown that by increasing the residence time of the drug in the nasal cavity, it is possible to increase the amount delivered to the brain. While mucoadhesives are effective at increasing brain concentrations, experiments combining their use with other formulation techniques have produced even greater brain uptake. The formulation composition appears to have a significant effect on drug uptake into the brain. However, as not all formulation strategies have shown to produce significant increases in brain delivery, there remains a need to improve the formulation design and standardization on in vitro and in vivo experimental conditions. By maximizing brain concentrations and limiting systemic exposure, this pathway offers the ability to decrease systemic side effects while producing therapeutic effects that otherwise would not be possible using other non-invasive routes of administration.

Despite these potential limitations, the nasal route of administration for brain delivery has shown promise for therapeutic efficacy based on animal models and clinical trials in humans[6,7] Existing methods and devices for administering therapeutic agents nasally include shortcomings that have not been adequately addressed. For example, traditional methods of therapeutic agent nasal administration utilize generic devices inserted into a subject's nasal cavity. Such generic devices do not account for unique anatomical structures of individual subjects. Accordingly, these differences in anatomical structures can affect the amount of therapeutic agent that is deposited to the olfactory region and can present challenges in nasally administering a desired dosage of a particular therapeutic agent.

Currently, many of the commercial nasal preparations are delivered with metered-dose pump sprays. Of the relatively small volume that is administrable utilizing metered-dose spray pumps, only around 2.5% is deposited in the area which corresponds to the olfactory region[8]. One of the oldest nasal delivery systems is nasal drops[9]. When administered properly, nasal drops spread over a larger area than nasal sprays, however, are often cleared faster than nasal sprays as well[10]. An important limitation of nasal drops is that their efficacy can be affected by patient administration technique, requiring complex maneuvers to achieve correct head positioning[9].

Successful targeting of nose-to-brain drug delivery requires a formulation to be administered in such a way that the amount deposited on the olfactory epithelium is maximized. Yet there are only a limited number of examples of such devices described in the art.

Many different delivery devices and methods have been developed in attempts to overcome the issues relating to targeting the olfactory region. Vianase™ is an electronic atomizer device developed by Kurve Technology® which consists of a nebulizer attached to a vortex chamber. Nebulized drug particles move in a vortex in the vortex chamber and continue to exhibit this flow when leaving the device[11]. This reportedly promotes a larger area for deposition compared to conventional pump nasal sprays, including deposition on the olfactory region.

The Opt-Powder device by Optinose® is a bi-directional delivery device which uses the patient's own exhalation force to emit the dose from the device. Closure of the soft palate ensures that none of the flowing powder can be deposited into the lungs. Djupesland and Skretting compared the deposition of radiolabeled lactose from the Opt-Powder device to the deposition of a radiolabeled liquid formulation from a conventional pump nasal spray in seven subjects. They report just over 18% of the powder from the Opt-Powder deposited in the upper region of the nasal cavity while only about 2.4% of the liquid from the spray was deposited in the same region[8].

There is presently a shortage of methods and devices that provide for effective nasal administration of therapeutic agents to treat diseases and disorder such as neurological pathologies to patients.

SUMMARY

Exemplary embodiments of the present disclosure address the issues described above. Exemplary embodiments include an apparatus for nasal administration of a pharmaceutical composition, where the apparatus comprises: a reservoir; a conduit in fluid communication with the reservoir; an actuator configured to transfer a pharmaceutical composition from the reservoir to the conduit and emit the pharmaceutical composition from the conduit; and an anatomic positioning device configured to position the conduit in a nasal cavity of a user.

In certain embodiments, the anatomic positioning device is modeled after anatomic features of an individual user. In particular embodiments, the anatomic positioning device is modeled after a computerized tomography (CT) scan of an individual user. In some embodiments, the anatomic positioning device is modeled after a magnetic resonance imaging (MRI) scan of a nasal cavity of an individual user. In specific embodiments, the anatomic positioning device comprises: an adjustable member coupled to the conduit, where:

the adjustable member can be adjusted to control a depth at which the conduit is inserted into the nasal cavity; and the adjustable member can be adjusted to control an angle at which the conduit is inserted into the nasal cavity.

In certain embodiments, the conduit is threaded and the adjustable member is threadably coupled to the conduit. In particular embodiments, the anatomic positioning device further comprises: a dial mechanism for controlling the depth and the angle at which the conduit is inserted into the nasal cavity. Some embodiments further comprise a sensor configured to detect an angle at which the conduit is positioned, and in specific embodiments the sensor is a mechanical sensor or an electronic sensor.

In specific embodiments, the anatomic positioning device comprises an anatomical nostril insert. In certain embodiments, the anatomic positioning device comprises an external frame structure. In particular embodiments, the external frame structure is configured to be placed outside a nose and configured to guide the conduit into the nasal cavity. In some embodiments, the actuator is configured to increase pressure in the reservoir. In specific embodiments, the actuator is configured to compress the reservoir.

In certain embodiments, the pharmaceutical composition comprises: (A) a therapeutic agent; and (B) a pharmaceutical excipient, where: the pharmaceutical composition is formulated for administration intranasally for delivery to the brain; and the pharmaceutical composition is formulated as a solid dispersion. In particular embodiments, the solid dispersion is amorphous. In some embodiments, the solid dispersion is in a nanocrystalline state. In specific embodiments, the therapeutic agent is a chemotherapeutic compound. In certain embodiments, the therapeutic agent is mebendazole. In particular embodiments, the pharmaceutical excipient is a polymer. In some embodiments, the pharmaceutical excipient is a polyvinylpyrrolidone copolymer. In specific embodiments, the pharmaceutical excipient is a polyvinylpyrrolidone and vinyl acetate copolymer. In certain embodiments, the pharmaceutical excipient is Kollidon® VA64.

In particular embodiments, the pharmaceutical composition comprises: (A) a therapeutic agent; and (B) a pharmaceutical excipient, where: the pharmaceutical composition is formulated for administration intranasally for delivery to the brain; and the pharmaceutical composition is formulated as a foam. In some embodiments, the pharmaceutical excipient is a composition comprising a first polymer and a second polymer. In specific embodiments, the first polymer is a polyether. In certain embodiments, the first polymer is a triblock polyether. In particular embodiments, the first polymer is a polyethylene-polypropylene-polyethylene polymer. In some embodiments, the first polymer is Poloxamer® 407. In specific embodiments, the therapeutic agent is a contrast agent. In certain embodiments, the therapeutic agent is perfluorooctylbromide. In particular embodiments, the pharmaceutical composition comprises an imaging agent. In some embodiments, the imaging agent is fluorescein. In specific embodiments, the pharmaceutical composition further comprises a basic solution. In certain embodiments, the basic solution is a hydroxide solution. In particular embodiments, the basic solution is a sodium hydroxide solution. In some embodiments, the pharmaceutical composition comprises a propellant. In specific embodiments, the propellant is a haloalkane$_{(C \leq 12)}$. In certain embodiments, the propellant is a haloalkane$_{(C \leq 6)}$. In particular embodiments, the propellant is 1,1,1,2,3,3,3-heptafluoropropane.

Certain embodiments, include a method of developing individualized administration of a pharmaceutical composition to a person, where the method comprises: obtaining one or more images of a nasal cavity of the person; creating a three-dimensional model of the nasal cavity; and determining person-specific parameters for a device configured to administer the pharmaceutical composition to the person, where the person-specific parameters are based on the three-dimensional model of the nasal cavity.

In particular embodiments, the one or more images comprise computed tomography (CT) scans of the nasal cavity of the person. In some embodiments, the three-dimensional model of the nasal cavity is created by image processing software utilizing the one or more images obtained of the nasal cavity of the person. In specific embodiments, the image processing software is segmentation software. In certain embodiments, the person-specific parameters include an administration angle of the device. In particular embodiments, the person-specific parameters include an insertion depth of the device. In some embodiments, the person-specific parameters include a head tilt angle. In specific embodiments, the person-specific parameters include an actuation force of the device. Certain embodiments, further comprise creating a three-dimensional casting of the nasal cavity from the three-dimensional model of the nasal cavity.

In particular embodiments, creating a three-dimensional casting of the nasal cavity comprises: obtaining computed tomography (CT) scans of the nasal cavity; using image processing software to generate cross-section views of the CT scans in the coronal, sagittal and axial positions; creating a three-dimensional model of the nasal cavity with the image processing software; and printing the three-dimensional casting from the three-dimensional model via stereolithography. In some embodiments, the three-dimensional casting is printed in multiple anatomical segments. In specific embodiments, the multiple anatomical segments include an anterior segment, an upper segment, a middle segment, a lower segment and a naso-pharynx segment. In certain embodiments, the three-dimensional model comprises a superior turbinate, a middle turbinate, and an inferior turbinate. In particular embodiments, the anterior segment comprises a boundary at a coronal slice made directly anterior to the superior turbinate, the middle turbinate, and the inferior turbinate. In some embodiments, the upper segment comprises a lower boundary between the superior turbinate and the middle turbinate. In specific embodiments, the middle segment comprises a first boundary between the middle turbinate and the superior turbinate and a second boundary between the middle turbinate and the inferior turbinate. In certain embodiments, the lower segment comprises an upper boundary between the inferior turbinate and the middle turbinate. In particular embodiments, a boundary of the naso-pharynx segment is a coronal slice made directly posterior to the superior turbinate, the middle turbinate, and the inferior turbinate.

Specific embodiments further comprise: (1) providing an initial administration of a test compound into the anterior segment of the three-dimensional casting; and (2) observing an initial amount of the test compound deposited in the upper segment of the three-dimensional casting after the initial administration of the test compound into the anterior segment. Certain embodiments, further comprise: (3) altering one or more parameters of the initial administration of the test compound into the anterior segment; (4) providing a subsequent administration of the test compound into the anterior segment of the three-dimensional casting; (5) observing a subsequent amount of the test compound deposited in the upper segment of the three-dimensional casting after the subsequent administration of the test compound into the anterior segment; (6) comparing the subsequent amount of the test compound deposited to the initial amount of the test compound deposited; and (7) repeating steps (3)-(6) to maximize the subsequent amount of the test compound deposited in the upper segment of the three-dimensional casting.

In certain embodiments, providing an initial administration of the test compound into the anterior segment comprises: inserting a device with a conduit into the anterior segment of the three-dimensional model; and directing the test compound from the conduit into the anterior segment. In particular embodiments, altering the one or more parameters comprises altering an insertion depth of the device into the anterior segment of the three-dimensional model. In some embodiments, altering the one or more parameters comprises altering an insertion angle of the device into the anterior segment of the three-dimensional model. In specific embodiments, the insertion angle is measured from a vertical reference line extending from a nostril of the anterior segment when viewed from the front. In certain embodiments, the insertion angle is measured from a vertical reference line extending from a nostril of the anterior segment when viewed from the side. In some embodiments, the test compound comprises a fluorescent agent. In specific embodiments, computer software is utilized to determine the person-specific parameters based on the three-dimensional model of the nasal cavity.

Certain embodiments include a pharmaceutical composition comprising: (A) a therapeutic agent; and (B) a pharmaceutical excipient, where: the pharmaceutical composition is formulated for administration intranasally for delivery to the brain; and the pharmaceutical composition is formulated as a solid dispersion. In particular embodiments, the solid dispersion is amorphous. In some embodiments, the solid dispersion is in a nanocrystalline state. In specific embodiments, the therapeutic agent is a chemotherapeutic compound. In certain embodiments, the therapeutic agent is mebendazole. In particular embodiments, the pharmaceutical excipient is a polymer. In some embodiments, the pharmaceutical excipient is a polyvinylpyrrolidone copolymer. In specific embodiments, the pharmaceutical excipient is a polyvinylpyrrolidone and vinyl acetate copolymer. In certain embodiments, the pharmaceutical excipient is Kollidon® VA64.

Particular embodiments include a pharmaceutical composition comprising: (A) a therapeutic agent; and (B) a pharmaceutical excipient, where: the pharmaceutical composition is formulated for administration intranasally for delivery to the brain; and the pharmaceutical composition is formulated as a foam. In some embodiments, the pharmaceutical excipient is a composition comprising a first polymer and a second polymer. In specific embodiments, the first polymer is a polyether. In certain embodiments, the first polymer is a triblock polyether. In particular embodiments, the first polymer is a polyethylene-polypropylene-polyethylene polymer. In some embodiments, the first polymer is Poloxamer® 407. In specific embodiments, the therapeutic agent is a contrast agent. In certain embodiments, the therapeutic agent is perfluorooctylbromide. In particular embodiments, the pharmaceutical composition comprises an imaging agent, and in certain embodiments the imaging agent is fluorescein.

In some embodiments, the pharmaceutical composition further comprises a basic solution. In specific embodiments, the basic solution is a hydroxide solution. In certain embodiments, the basic solution is a sodium hydroxide solution. Some embodiments further comprise a propellant. In specific embodiments, the propellant is a haloalkane$_{(C \leq 12)}$. In certain embodiments, the propellant is a haloalkane$_{(C \leq 6)}$. In particular embodiments, the propellant is 1,1,1,2,3,3,3-heptafluoropropane.

Specific embodiments include a method of delivering a pharmaceutical composition to a subject, where the method comprises: inserting an apparatus into a nasal cavity of the subject, wherein the apparatus is anatomically modeled after the nasal cavity of the subject; and emitting the pharmaceutical composition from the apparatus into the nasal cavity of the subject.

Certain embodiments include a method of delivering a pharmaceutical composition to a subject, where the method comprising: inserting an apparatus according to the present disclosure into a nasal cavity of the subject; and emitting the pharmaceutical composition from the apparatus into the nasal cavity of the subject.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "approximately, "about" or "substantially" mean, in general, the stated value plus or minus 10%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE FIGURES

FIG. 21 illustrates a coronal plane CT slice of a nasal cavity.

FIG. 22 illustrates a sagittal plane CT slice of a nasal cavity.

FIGS. 23A-B illustrate a schematic of a testing apparatus of a nasal cavity.

FIG. 24 illustrates a schematic of administration angles and deposition efficiency.

DETAILED DESCRIPTION OF ILLUSTRATIVE EMBODIMENTS

Figure 1:
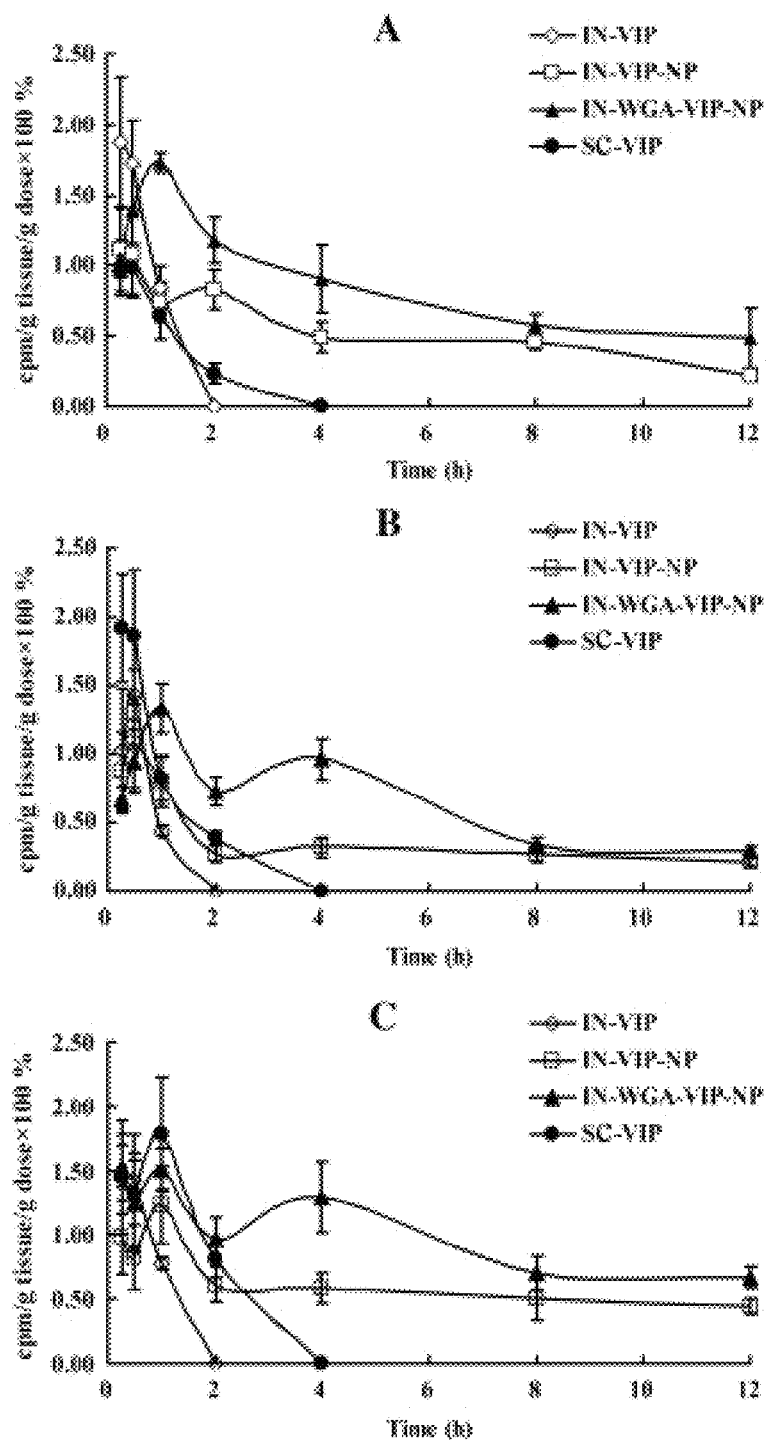
FIGS. 1A-C illustrate graphs of amount vs. time profiles for vasoactive intestinal peptide after intranasal administration in the olfactory bulb and olfactory tract (A), cerebrum (B) and cerebellum (C). (Reprinted with permission from Gao et al., 2007).

The present disclosure provides an apparatus that may be used to deliver a pharmaceutical composition to specific locations of the nasal cavity. The apparatus may preferably be formed using a subject's own imaging scans of the nasal cavity to prepare an anatomically formulated apparatus and the composition contained in the apparatus for delivering the pharmaceutical composition to the brain via the nasal cavity. Also, provided herein are compositions which are formulated as solid dispersions that can be administered to the nasal cavity for delivery to the brain. In particular, these compositions may show beneficial properties such as increased concentrations when formulated or improved absorption into the brain.

A. Anatomical Intranasal Delivery Device

Provided herein are intranasal delivery devices which have been anatomically formed to deliver the therapeutic agent to specific areas of the nasal cavity. In order to properly form the intranasal delivery device, it is important to understand the general anatomy of the naval cavity.

i. Nasal Cavity Anatomy

The nasal cavity is defined by three main regions: the vestibule, olfactory region and the respiratory region. The respiratory region comprises the largest surface area of the nasal cavity and makes up a majority of the posterior area of the nasal cavity.[12] The olfactory region is located at the roof of the nasal cavity and makes up nearly 10% of the total 150 cm$^2$ surface area.[13] The different regions in the nasal cavity have varying epithelial layers which help support their individual functions. The respiratory epithelium is comprised of ciliated and non-ciliated columnar cells. The ciliated cells of the respiratory region contain hair-like extensions that beat at 1000 strokes per minute in a single direction to clear particles towards the nasopharynx region. This process is known as the mucociliary clearance.[13] The olfactory epithelium is comprised of supporting cells and olfactory receptor neurons which are responsible for our sense of smell.[14] The cilia found in the olfactory region are non-motile since they lack the dynein arms required for movement.[15] For a more detailed discussion of the nasal cavity anatomy the reader is referred to Clerico et al.[16], Mygind et al.[17] and Thomas et al.[12]

While much of the initial studies on this manner of delivery has been carried out in animals, there are important anatomical differences between the typically studied animal models and humans that are expected to be important when predicting the expected response in humans. The nasal cavity of rats is composed of about 50% olfactory epithelium, which makes up around 6.75 cm$^2$. In mice the olfactory epithelium makes up about 47% of the nasal cavity, which is about 1.37 cm$^2$. This is much larger than the 8-10% of the nasal cavity that is comprised of olfactory epithelium in humans. This makes up around 12.5 cm$^2$, although the olfactory epithelium area can vary slightly from person-to-person.[18,19] The location of the olfactory epithelium in humans may also add additional challenges to drug delivery. For effective brain targeting by the intranasal route, drug needs to be delivered to the olfactory epithelium. This may require specialized delivery devices, or subject positioning, that are designed to maximize this deposition pattern. For all of these reasons, Ruigrok and Lange[18] expect that nose-to-brain delivery in humans is overestimated based on animal studies, especially those conducted in rats. Ruigrok and Lange[18] explained that pharmacodynamic-pharmacokinetic studies in animals may provide better predictive models for assessing drugs undergoing direct nose-to-brain transport in humans.

Exemplary embodiments of the present disclosure comprise methods and apparatus for delivering a pharmaceutical composition to a subject. In exemplary embodiments, the method comprises inserting an apparatus that is anatomically modeled after the nasal cavity of the subject into the nasal cavity of the subject. Exemplary methods further comprise emitting the therapeutic agent from the device into the nasal cavity of the subject. Exemplary embodiments further comprise methods for developing individualized administration of a pharmaceutical composition to a person.

Figure 3:
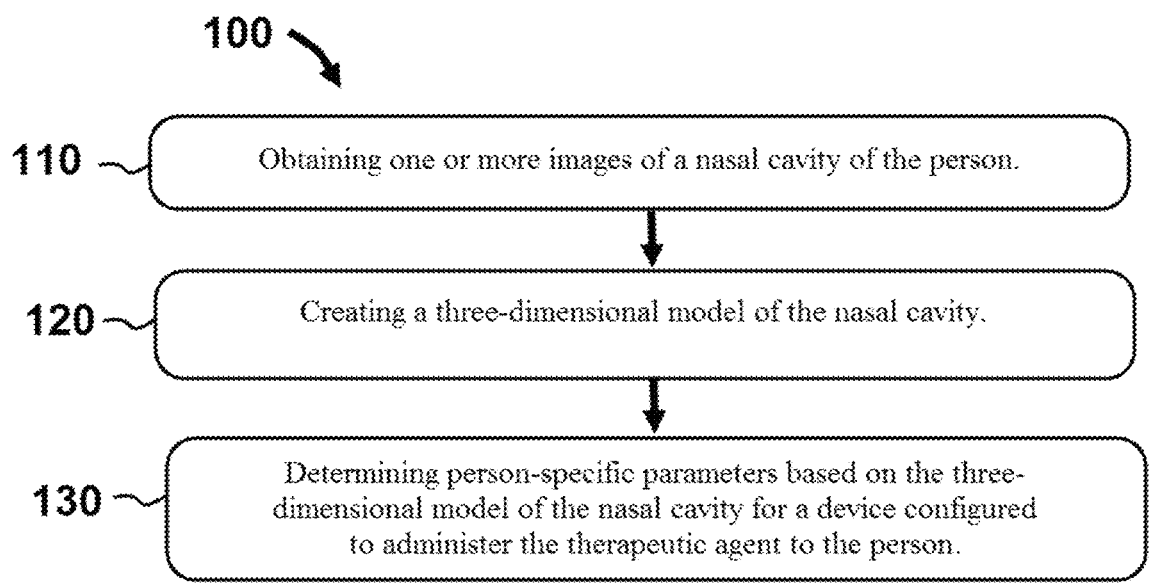
FIG. 3 illustrates a flowchart of steps performed in an exemplary method for developing individualized administration of a pharmaceutical composition to a person.
Figure 4:
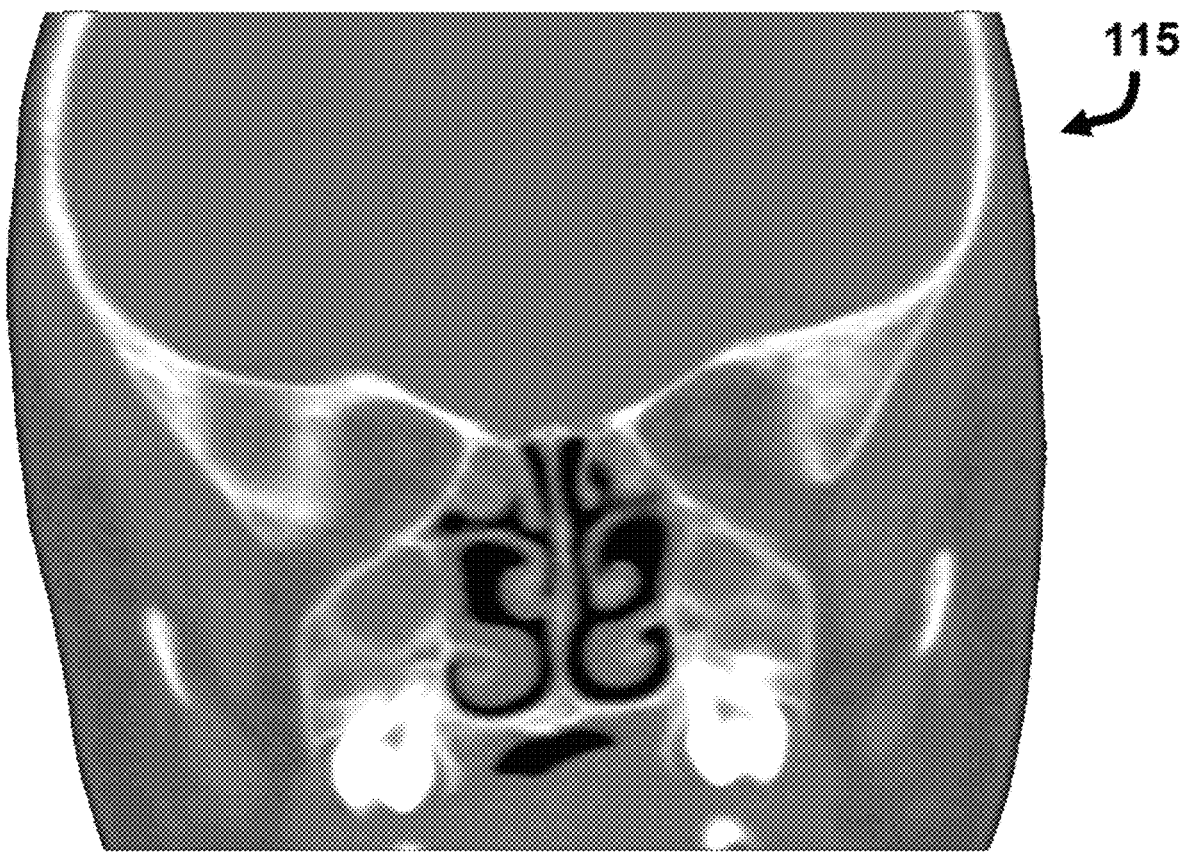
FIG. 4 illustrates a computed tomography (CT) scan of a nasal cavity.
Figure 5:
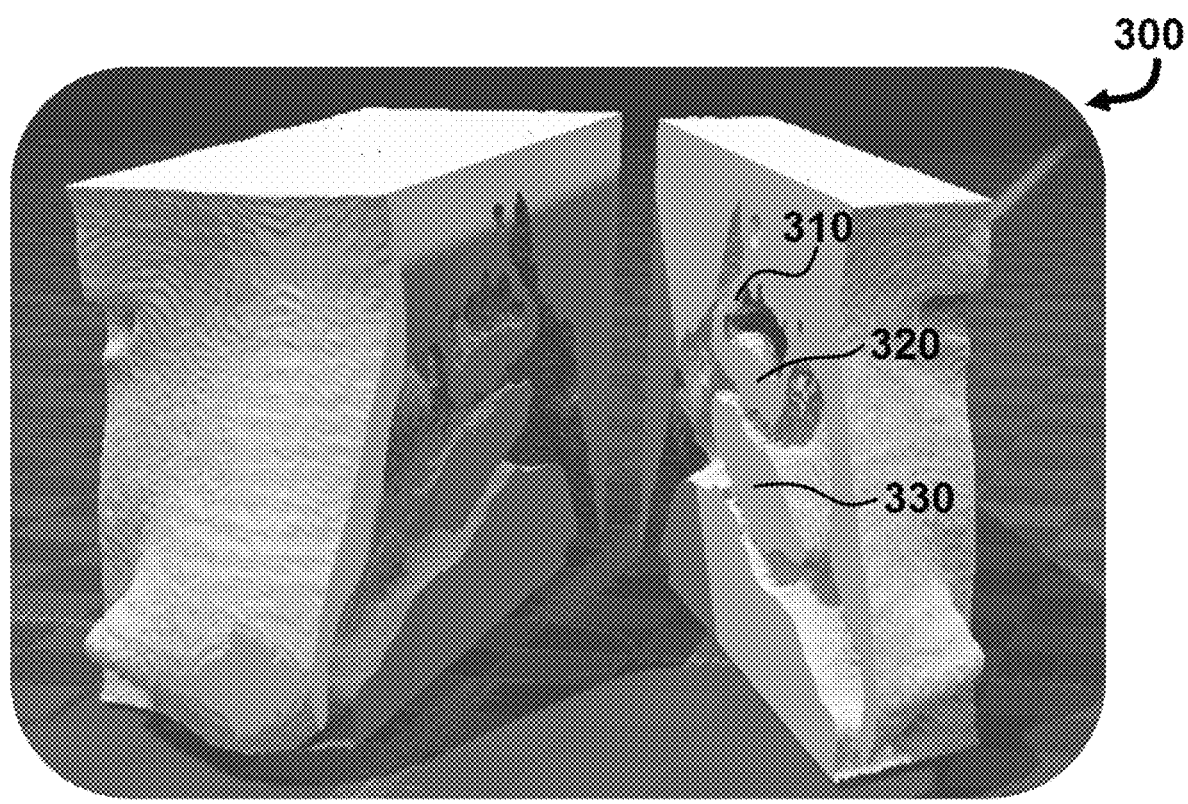
FIG. 5 illustrates a three-dimensional model of a nasal cavity in a section view.

Referring now to FIG. 3, a flowchart of steps is shown performed in an exemplary method 100 for developing individualized administration of a pharmaceutical composition to a person. In this embodiment, method 100 comprises a first step 110 of obtaining one or more images of a nasal cavity of the person. In certain embodiments, the images may comprise magnetic resonance imaging (MRI) scans or computed tomography (CT) scans. One example of such a nasal cavity image from a CT scan is shown in FIG. 4 as image 115. Referring back now to FIG. 3, method 100 may also comprise a second step 120 of creating a three-dimensional model of the nasal cavity (e.g. by converting the images obtained in step 130 into a three-dimensional model). One example of such a three-dimensional model 300 in a section view is illustrated in FIG. 5. As shown in FIG. model 300 comprises a superior turbinate 310, a middle turbinate 320, and an inferior turbinate 330.

As shown in FIG. 3, step 130 comprises determining person-specific parameters (based on three-dimensional model 300 of the nasal cavity) for a device configured to administer the therapeutic agent to the person. In certain embodiments, three-dimensional model 300 of the nasal cavity can be created by image processing software (e.g. segmentation software) utilizing the one or more images obtained of the nasal cavity of the person.

As explained in further detail below, the person-specific parameters may include an administration angle, insert depth, and/or an actuation force of the device. The person-specific parameters may also include a head tilt angle of the person during administration of the therapeutic agent.

In certain embodiments, the method may include creating a three-dimensional casting of the nasal cavity from the three-dimensional model of the nasal cavity. For example, the three-dimensional casting can be created by printing three-dimensional model 300 via stereolithography. In specific embodiments, computed tomography (CT) scans of the nasal cavity can be obtained and image processing software used to generate cross-section views of the CT scans in the coronal, sagittal and axial positions. The image processing software can then create the three-dimensional model of the nasal cavity that can be printed via stereolithography.

Figure 6:
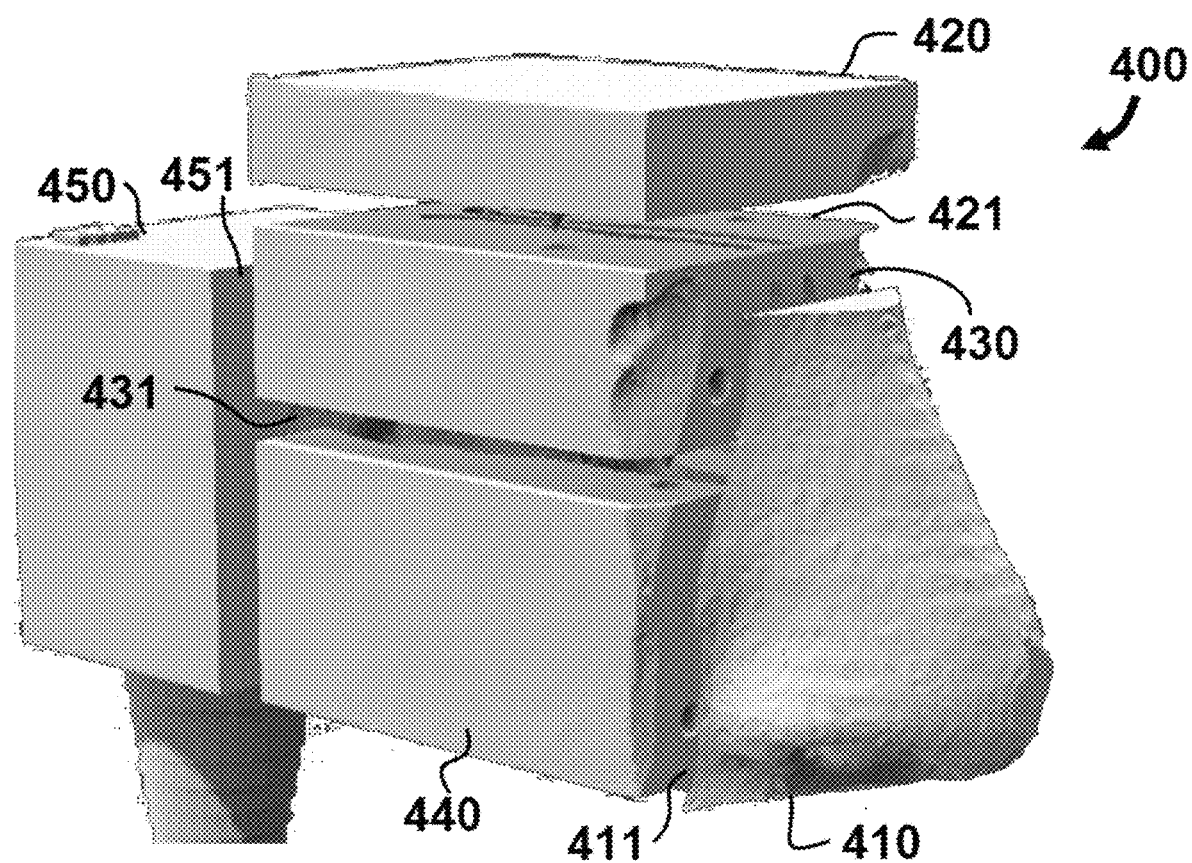
FIG. 6 illustrates a three-dimensional casting of a nasal cavity printed in multiple anatomical segments.

Referring now to FIG. 6, one example of a three-dimensional casting 400 is shown printed in multiple anatomical segments. In this embodiment, casting 400 comprises an anterior segment 410, an upper segment 420, a middle segment 430, a lower segment 440 and a naso-pharynx segment 450. Anterior segment 410 comprises a boundary 411 at a coronal slice made directly anterior to the superior turbinate, the middle turbinate, and the inferior turbinate (shown in FIG. As shown in FIG. 6, upper segment 420 comprises a lower boundary 421 between the superior turbinate and the middle turbinate. In addition, middle segment 430 comprises boundary 421 and a boundary 431 between the middle turbinate and the inferior turbinate (e.g. middle segment is located between boundaries 421 and 431). Furthermore, lower segment 440 comprises boundary 431 (e.g. lower segment 440 is located below boundary 431). Finally, naso-pharynx segment 450 comprises a boundary 451 at a coronal slice made directly posterior to the superior turbinate, the middle turbinate, and the inferior turbinate.

Figure 7:
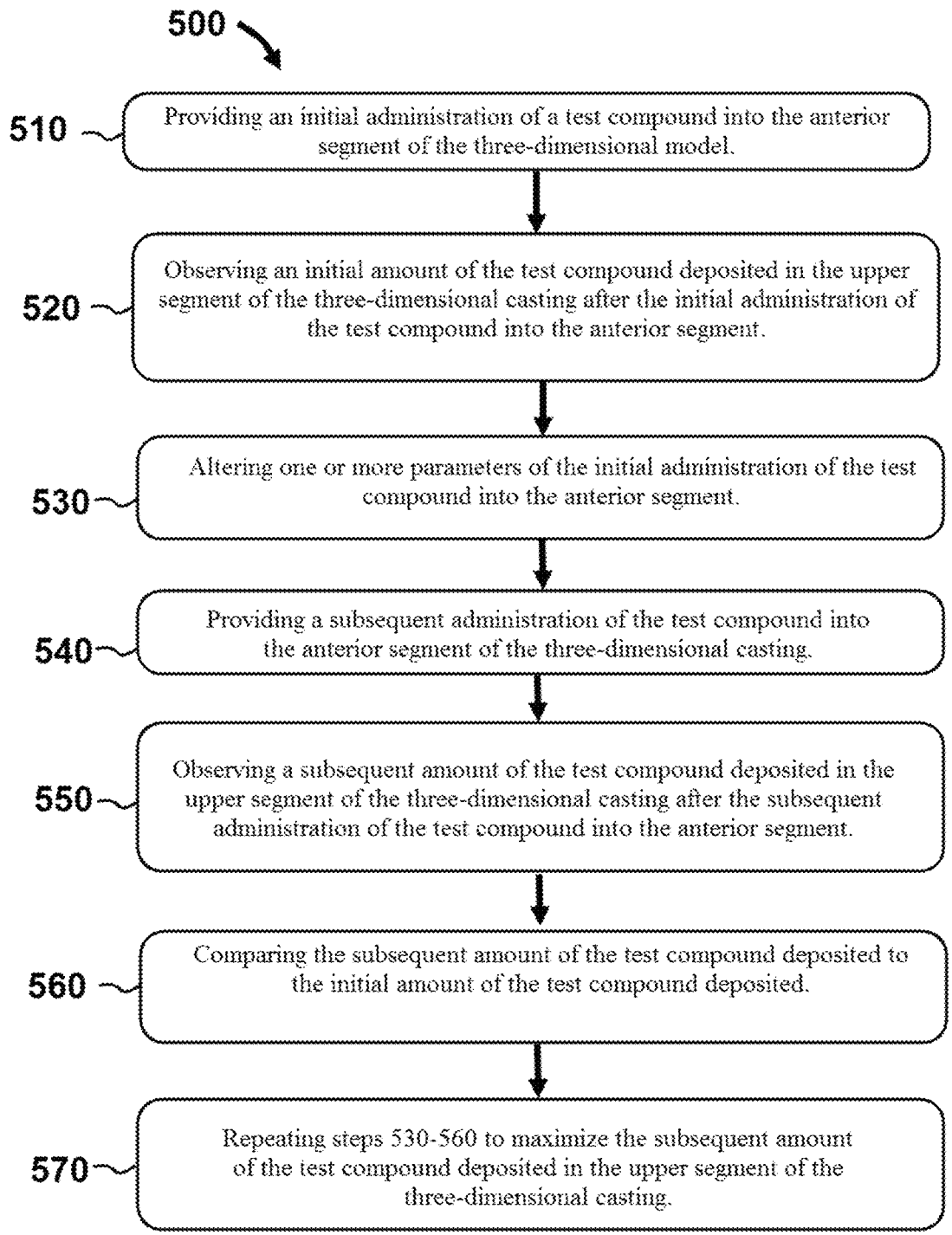
FIG. 7 illustrates a flowchart of steps performed in an exemplary method to determine the person-specific parameters used for individualized administration of a pharmaceutical composition to a person.

In certain embodiments, simulations via computer software can be used to determine the person-specific parameters used to administer the therapeutic agent. In other embodiments, experimental testing can be performed on casting 400 to determine the person-specific parameters used to administer the therapeutic agent. For example referring now to FIG. 7, a method 500 comprises a first step 510 of providing an initial administration of a test compound into the anterior segment of the three-dimensional casting. Method 500 also comprises a second step 520 of observing an initial amount of the test compound deposited in the upper segment of the three-dimensional model after the initial administration of the test compound into the anterior segment. This initial amount of the test compound deposited can then be compared to subsequent amounts using different parameters, as explained further below.

For example, method 500 can include third and fourth steps 530 and 540 comprising altering one or more parameters of the initial administration of the test compound into the anterior segment and providing a subsequent administration of the test compound into the anterior segment of the three-dimensional model. Step 550 comprises observing a subsequent amount of the test compound deposited in the upper segment of the three-dimensional casting after the subsequent administration of the test compound into the anterior segment. In step 560, the subsequent amount of the test compound deposited can be compared to the initial amount of the test compound deposited. Steps 530-560 can be repeated to maximize the subsequent amount of the test compound deposited in the upper segment of the three-dimensional casting.

Figure 8:
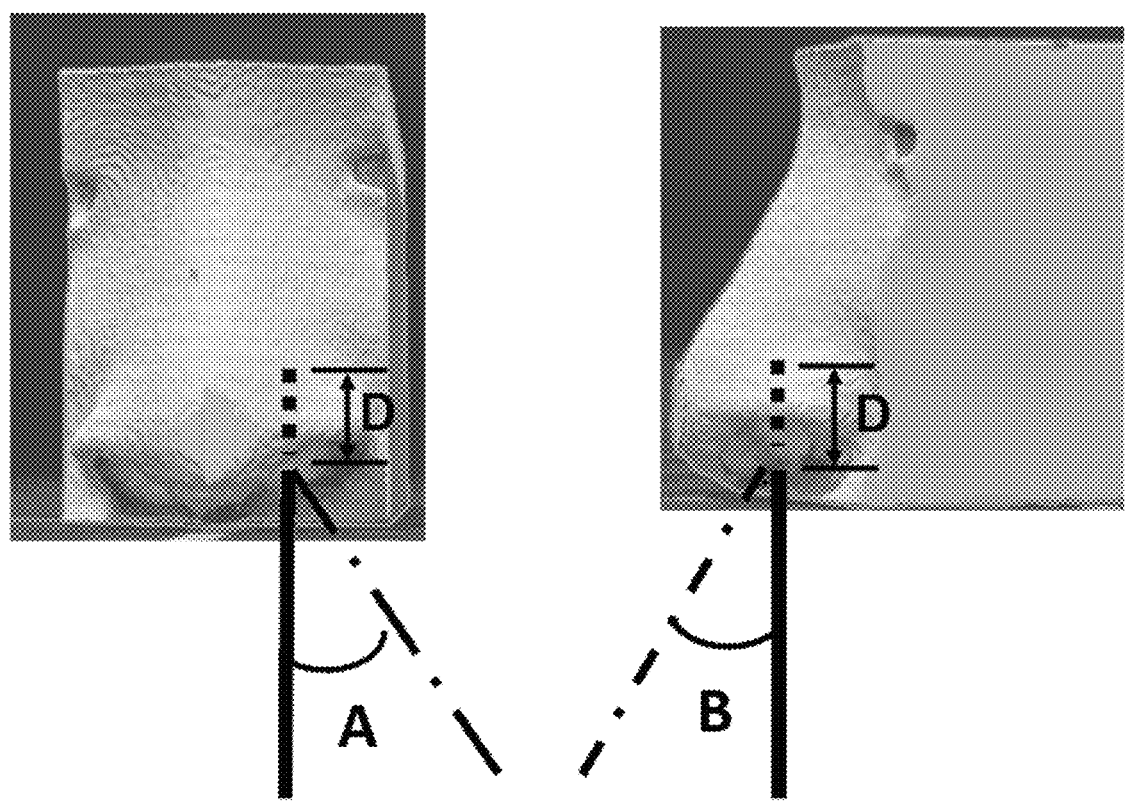
FIG. 8 illustrates insertion angles and an insertion depth of an apparatus used in the individualized administration of a pharmaceutical composition to a person.

For example, administration of the test compound into the anterior segment may comprise inserting a device with a conduit into the anterior segment of the three-dimensional model, and directing the test compound from the conduit into the anterior segment. If the insertion depth of the device is decreased in a subsequent administration and the test compound deposited is also decreased, the insertion depth can be increased in further administrations in an effort to maximize the amount of the test compound deposited in the upper segment. Similarly, the angle at which a device is inserted into the anterior segment can be altered based on the comparison of the amount of the test compound deposited. Referring now to FIG. 8, an insertion depth D is shown as well as insertion angles A and B used during administration. As shown in FIG. 8 insertion angle A is measured from a vertical reference line extending from a nostril of the anterior segment when viewed from the front. Insertion angle B is measured from a vertical reference line extending from a nostril of the anterior segment when viewed from the side.

Figure 9:
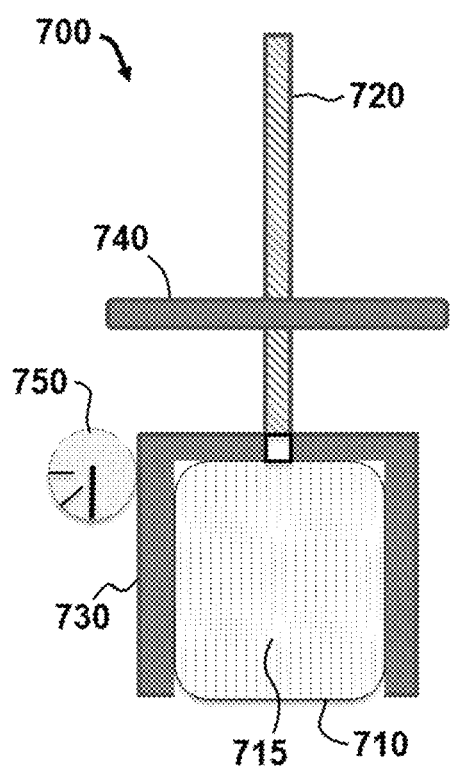
FIG. 9 illustrates a schematic of an apparatus used in the individualized administration of a pharmaceutical composition to a person according to a first exemplary embodiment.

Certain embodiments also include an apparatus for nasal administration of therapeutic agents. Referring now to FIG. 9, an apparatus 700 comprises a reservoir 710 containing a pharmaceutical composition 715, and a conduit 720 in fluid communication with reservoir 710. Apparatus 700 can also comprise an actuator 730 configured to transfer pharmaceutical composition 715 from reservoir 710 to the conduit 720 and emit pharmaceutical composition 715 from conduit 720.

In addition, apparatus 700 may comprise an anatomic positioning device 740 configured to position conduit 720 in a nasal cavity of a user (e.g., in a manner shown in FIG. 8) in a way to maximize the amount of pharmaceutical composition 715 deposited in the upper segment of the nasal cavity. Anatomic positioning device 740 can comprise dimensions or features that are obtained based on experimental testing of castings or computer simulation of models based on specific features of the subject nasal cavity.

Figure 10:
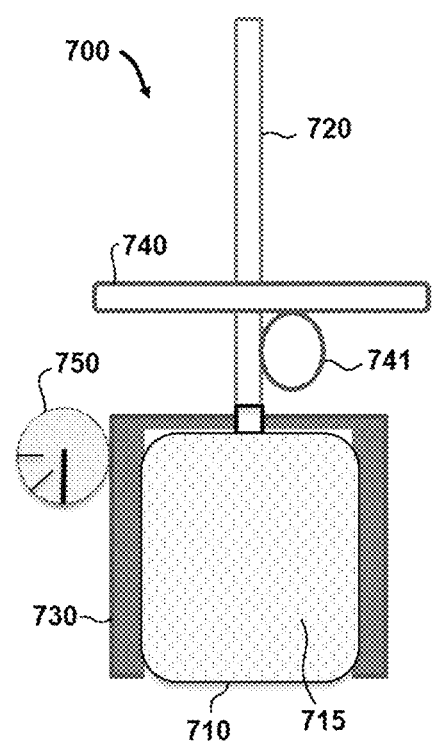
FIG. 10 illustrates a schematic of an apparatus used in the individualized administration of a pharmaceutical composition to a person according to a second exemplary embodiment.
Figure 11:
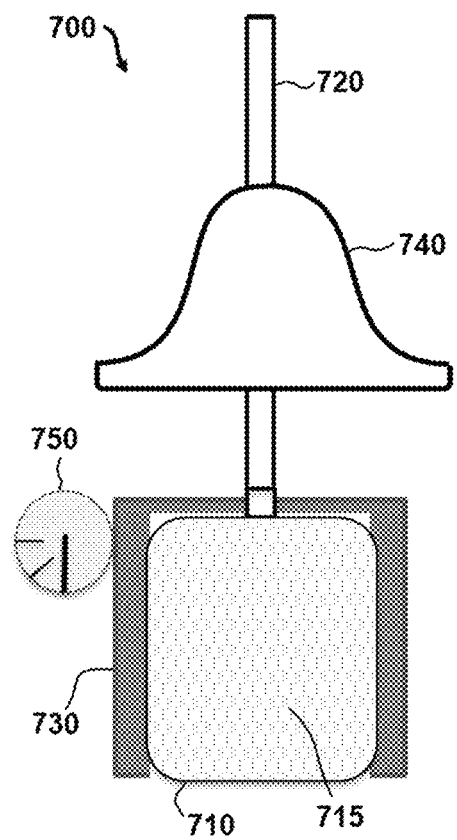
FIG. 11 illustrates a schematic of an apparatus used in the individualized administration of a pharmaceutical composition to a person according to a third exemplary embodiment.
Figure 12:
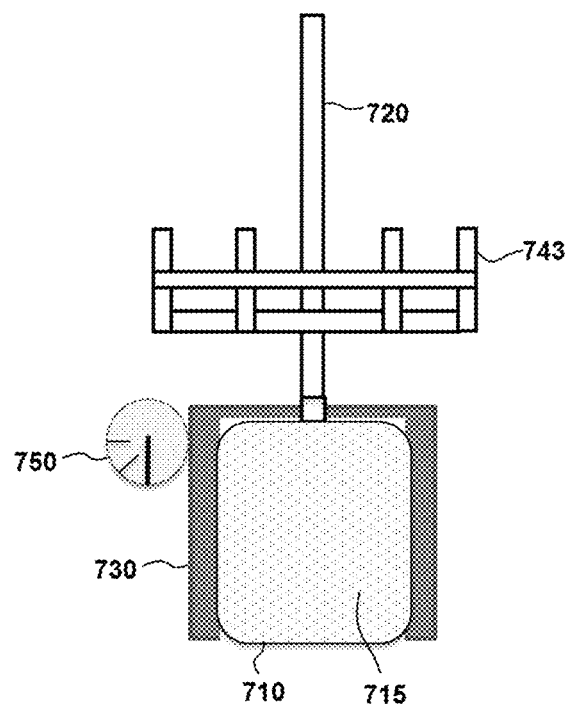
FIG. 12 illustrates a schematic of an apparatus used in the individualized administration of a pharmaceutical composition to a person according to a fourth exemplary embodiment.
Figure 13:
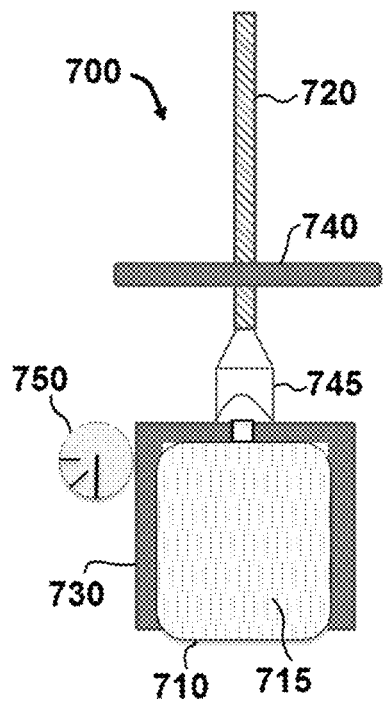
FIG. 13 illustrates a schematic of an apparatus used in the individualized administration of a pharmaceutical composition to a person according to a fifth exemplary embodiment.

In certain embodiments, anatomic positioning device 740 can be modeled after anatomic features of an individual user, including for example, the shape of the anterior segment of the nasal cavity. In particular embodiments, anatomic positioning device 740 may comprise an adjustable member coupled to conduit 720 that can be adjusted to control a depth and/or an angle at which the conduit 720 is inserted into the nasal cavity. In specific embodiments, conduit 720 is threaded and the adjustable member is threadably coupled to conduit 720. Apparatus 700 may also comprise a mechanical or electronic sensor 750 configured to detect an angle at which the conduit 720 is positioned. As shown in FIG. 10, in certain embodiments anatomic positioning device 740 may comprise a dial mechanism 741 for controlling the depth and the angle at which conduit 720 is inserted into the nasal cavity. As shown in FIG. 11, in particular embodiments, anatomic positioning device 740 may comprise an anatomical nostril insert 742. Referring now to FIG. 12, in other embodiments, anatomic positioning device may comprise an external frame structure 743 that is configured to be placed outside a nose and configured to guide conduit 720 into the nasal cavity. As shown in FIG. 13, certain embodiments may comprise a chamber 745 for loading a dose-containing portion of formulation.

Figures 14, 15:
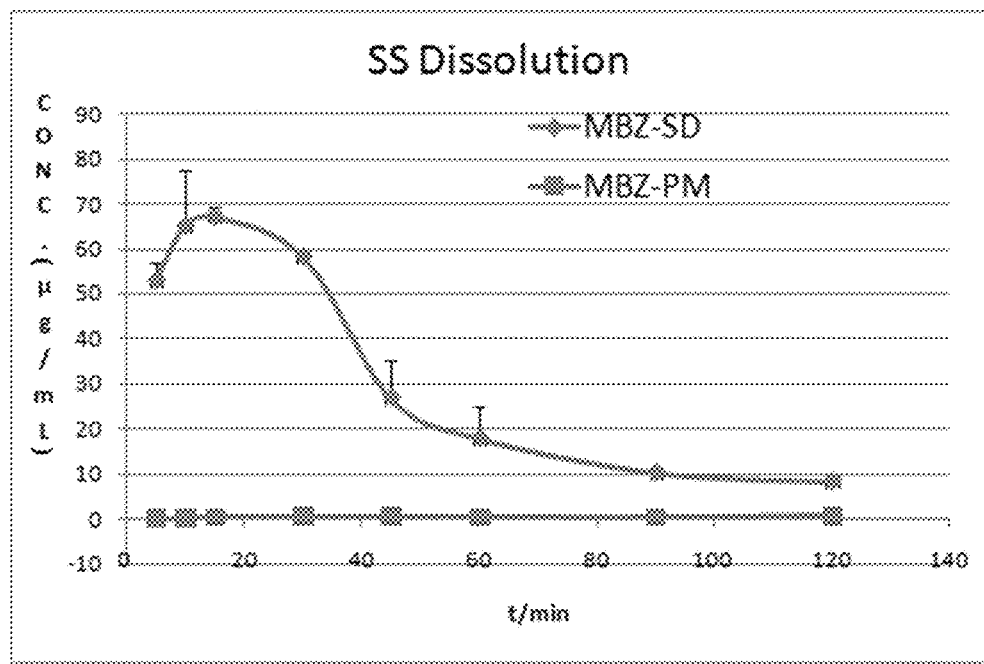
FIG. 14 illustrates a table showing administration angle and percent deposition in an upper region of a nasal cavity.
FIG. 15 illustrates a graph of concentration of a solid dispersion powder formulation for personalized delivery to the olfactory region of a human.

Referring now to FIG. 14, a table illustrates how angle optimization can affect deposition of a test compound in the upper region of a three-dimensional cast (e.g. upper segment 420 shown in FIG. 6). In the table, "Angle A" and "Angle B" refer to the angles shown in FIG. 8. As shown in FIG. 14, an "A" angle of 7 degrees and a "B" angle of 23 degrees resulted in the maximum amount of the test compound deposited in the upper segment of the cast.

B. Pharmaceutical Compositions for Use in Intranasal Device

In some aspects, the present disclosure provides pharmaceutical compositions comprising a therapeutic agent and a pharmaceutical excipient. In certain embodiments, the pharmaceutical composition is formulated as a solid dispersion or foam, and is formulated for administration intranasally for delivery to the brain. Because navigating the human nasal cavity to target the upper region can be difficult, foam formulation can provide certain advantages by expanding to fill the target region of the nasal cavity.

i. Solid Dispersions

These compositions may contain a solid dispersion which is a mixture of an excipient and a therapeutic agent where these components are mixed at the solid state which has been prepared using a melting, solvent, or combination method. These compositions are known to increase the solubility of poorly soluble drugs, reduce the particle size, improve the wettability, improve the porosity of the drug, mask the taste, or decrease the amount of crystalline forms of the drug in the composition. Several methods of preparing solid dispersions are known to a person of skill in the art and contemplated herein.[20-26]

ii. Foam Formulations

It is also contemplated that the therapeutic agent may be formulated as a foam. A pharmaceutical foam is an emulsion which contains one or more therapeutic agents along with a surfactant, a liquid and/or a propellant. These compositions are classified as aerosols, which may be used to direct the therapeutic agent towards a specific area within the nasal cavity. These foam compositions may be formulated with the therapeutic agent as a solid dispersion. Foam formulations may incorporate nanoparticulate, suspension, solubilized and emulsion type dosage forms in exemplary embodiments. Foam compositions often may have an added benefit of increasing the concentration of the therapeutic agent or increasing the resident time of the composition within the nose. Methods of preparing foam formulations are taught by Arzhavitina and Steckel[27] and Zhao et al.[28-30]

iii. Other Pharmaceutical Compositions

In addition to the solid dispersion formulations and foam compositions prepared herein, the device used herein may also be used with other pharmaceutical compositions which have been prepared in the art. Table 1 provides a list of non-limiting examples that have so far been reported in the literature on formulations and their effects on nose-to-brain delivery. As can be seen in Table 1 below, formulations that have so far been utilized to enhance nose-to-brain delivery include: solutions, microemulsion, mucoadhesive formulations, polymeric nanoparticles, lipid-based nanoparticles as well as novel combination therapies. As would be known to a person of skill in the art, the choice of the formulation may be greatly influenced by the physicochemical properties of the drug.

TABLE 1

Drugs and Their Formulations Reported for Nose-to-Brain Delivery

| Drug | Formulation | Animal Model | Disease State Being Treated | Results | Reference |
|---|---|---|---|---|---|
| 5-FU | Solution | Rats pre-dosed with acetazolamide | CNS malignancy | 104% increased brain uptake compared to i.v. | 31 |
| Bromocriptine | Chitosan Nanoparticles | Mice | Parkinson's Disease | Showed significant increase in dopamine levels | 32 |

TABLE 1-continued

Drugs and Their Formulations Reported for Nose-to-Brain Delivery

| Drug | Formulation | Animal Model | Disease State Being Treated | Results | Reference |
|---|---|---|---|---|---|
| Buspirone | Chitosan/HP-β-CD solution | Rats | Depression | DTE-4.13 compared with 3.38 for i.n. plain solution | 33 |
| Carbamazepine | Hypromellose/Carbopol Gel | Rats | Epilepsy | Significantly higher brain uptake compared to i.v. | 34 |
| Carbamazepine | Thermoreversible Gel | Mice | Epilepsy | DTE - 0.98 i.n. and i.v. provide similar blood/plasma ratios | 35 |
| Curcumin | In Situ Gelling Microemulsion | Rats | Brain tumor/Alzheimer's Disease | DTE-6.5 | 36 |
| Donepezil | Chitosan Nanoparticles | Rats | Alzheimer's Disease | Significantly higher brain concentrations from nanoparticles | 37 |
| Doxepin | Thermoreversible Gel | Mice | Depression | No difference in pharmacodynamic endpoint | 38 |
| Duloxetine | Lipid Nanocarrier | Rats | Depression | DTE - 757.14% compared to 287.34% from solution | 39 |
| Estradiol | Cyclodextrin | Rats | Alzheimer's Disease | $AUC_{CSF}/AUC_{plasma}$ 1.60 which was significantly higher than 0.61 from i.v. | 40 |
| GDF-5 | Microemulsion | Rats | Parkinson's Disease | Significantly higher midbrain concentrations compared to acidic solution | 41 |
| Methotrexate | Mucoadhesive Solution | Rats pre-dosed with acetazolamide | CNS malignancy | 195% increase in uptake compared to i.n. without acetazolamide; 75% reduction in brain tumor weight | 42 |
| Methotrexate | Solution | Rats | CNS malignancy | DTE- 21.7% | 43 |
| Morphine | Solution (PBS buffer at pH 7.4) | Rats | Pain | Brain/Plasma AUC ratio of 3 after i.n. use and 0.1 after i.v. use | 44 |

TABLE 1-continued

Drugs and Their Formulations Reported for Nose-to-Brain Delivery

| Drug | Formulation | Animal Model | Disease State Being Treated | Results | Reference |
|---|---|---|---|---|---|
| Nimodipine | Microemulsion | Rats | Stroke, reduce dementia | Higher AUC in olfactory bulb but lower AUC in rest of brain after i.n. compared with i.v. treatment | 45 |
| Olanzapine | Nanomicellar Carrier | Rats | Schizophrenia/ Bi polar Disorder | DTE-520.26% | 46 |
| Olanzapine | PLGA Nanoparticles | Rats | Schizophrenia/ Bi polar Disorder | 10.86 times higher brain uptake compared to i.n. solution alone | 47 |
| Olanzapine | Mucoadhesive Nanoemulsion | Rats | Schizophrenia/ Bi polar Disorder | DTE-890% compared to 550% from i.n. solution | 48 |
| Paliperidone | Mucoadhesive Microemulsion | Rats | Schizophrenia/ Bi polar | DTE-320.69%; 1.74-fold higher than nasal solution alone | 49 |
| Raltitrexed | Solution (PBS pH 8) | Rats | CNS malignancy | DTE for Olfactory Bulb, Cerebrum and cerebellum was 127, 120 and 71 respectively | 50 |
| Rasagiline | Thermosensitive Gel | Rabbits | Parkinson's Disease | Significant improvement in brain uptake from gel formulations | 51 |
| Remoxipride | Solution (Normal Saline) | Rats | Psychosis | ~50% increase in brain/plasma AUC | 52 |
| Risperidone | Mucoadhesive Nanoemulsion | Rats | Schizophrenia/ Bi polar Disorder | DTE-476% | 53 |
| Risperidone | Solid Lipid Nanoparticles | Mice | Schizophrenia/ Bi polar Disorder | 10-fold higher brain AUC compared to i.v. solution | 54 |
| Ropinirole | Temperature sensitive in situ gel with Chitosan and HPMC | Rats | Parkinson's Disease | DTE-10.4 compared to 5.3 for solution alone | 55 |
| Saquinavir | Nanoemulsion | Rats | CNS involved HIV infection | ~62 times higher drug accumulation compared to i.v. suspension | 56 |
| Tacrine | Solution of Propylene glycol and Normal Saline | Mice | Alzheimer's Disease | DTE-207.23% | 57 |
| Tacrine | Mucoadhesive Microemulsion | Mice | Alzheimer's Disease | DTE-295.87% | 58 |

TABLE 1-continued

Drugs and Their Formulations Reported for Nose-to-Brain Delivery

| Drug | Formulation | Animal Model | Disease State Being Treated | Results | Reference |
|---|---|---|---|---|---|
| Testosterone | Noseafix ® Mucoadhesive system | Mice | CNS Hormone Replacement | Significantly higher brain levels except frontal cortex | 59 |
| UH-301 | Solution (Normal Saline) | Rats | Depression | No difference in CSF concentrations between i.n. or i.v. | 60 |
| Zidovudine-prodrug | Solid Lipid Microparticles | Rats | CNS involved HIV infection | 6-fold higher CSF uptake | 61 |
| Zolmitriptan | Micellar Nanocarrier | Rats | Migraine | Significant increase brain concentrations as soon as 30 min. up to 120 min. | 62 | i. Solution Based Formulations

In some aspects, it is contemplated that the instant intranasal delivery devices may be used with compositions which are formulated as a solution. When formulating drugs as a solution such as a molecular dispersion for use herein, the physicochemical properties of the drug will be the driving factor for absorption. Studies on direct nose-to-brain delivery with solutions have taken place on a number of drugs, as can be seen in Table 1; including elements like manganese[63,64] and cobalt,[65] to more complex small molecules like remoxipride[52] and UH-301[60], and even proteins[6,66,67]. Formulations reported by Kandimalla et al. showed that passive diffusion plays a role in the delivery of small lipophilic molecules through diffusion cell permeability studies with hydroxyzine.[69] Pardeshi et al.[15] compared the delivery of dopamine[70], a small molecule, to that of nerve growth factor, a small secreted protein (MW=26,500 Da), and observed that brain concentrations were fivefold higher for dopamine than the protein when dosed at the same concentration. Even though small lipophilic drugs are found to have the highest brain levels after intranasal administration, formulations with hydrophilic drugs often show the largest improvement in brain levels compared to other routes of administration. Raltitrexed, a hydrophilic small molecule with a log P of −0.98, was studied to assess brain levels after intranasal and intravenous administration. It was found that, depending on the section of brain, a 54-121 fold increase in the AUC was found after intranasal use compared to intravenous use in rats.[50] Wang et al. performed similar experiments with methotrexate, another hydrophilic drug with log P−1.98, and found that it provided greater than 13 fold higher CSF AUC after nasal administration compared to intravenous administration.[43] When comparing the CSF concentrations from the Wang et al. study to those that use a brain tumor model[42], it can be inferred that the increase in CSF concentration may be sufficient for pharmacological activity.

Remarkably, the nose-to-brain route also seems applicable to macromolecules[15,71] as evidenced by animal studies with plasmids[72], IGF-I[67] and Nerve Growth Factor[4]. Research with arginine vasopressin[73], insulin[7], oxytocin[6] and melanocortin melanocyte-stimulating hormone/adrenocorticotropin$_{4-10}$[74] supports the delivery of macromolecules in humans. While only a limited number of the current studies in humans provide pharmacokinetic evidence for the paracellular drug transportation pathway, many of the experiments have compared pharmacodynamic endpoints after intranasal and intravenous administration. Pietrowsky et al.[73] reported the event-related potentials, which are a measure of the brain's electrical response to a stimulus, after administration with either intranasal or intravenous arginine vasopressin. In a double-blind crossover study, subjects had a significant increase in the P3 component, the component of the event-related potentials that is task related, after intranasal administration, while intravenous administration did not show significant differences compared to placebo. Additionally, the plasma concentrations after intravenous administration were higher than that after intranasal use, which led Pietrowsky et al. to conclude that the peptide was delivered in a direct nose-to-brain transport pathway, and not merely being absorbed systemically and crossing the BBB. In rats, substances as large as mesenchymal stem cells have been delivered by direct nose-to-brain pathways[75]. The wide variety of substances that can be transported to the brain through these mechanisms gives promise to many treatment options for CNS-related disorders.

ii. Mucoadhesive/Viscosity Increasing Agents

Additionally, the intranasal administration methods and devices described herein may be used with different formulation techniques have been reported to overcome some of the barriers to nasal drug delivery in hopes of increasing the amount delivered to the brain. A large barrier that is unique to nasal delivery is the mucociliary clearance. Mucoadhesive and viscosity increasing agents have been used to increase drug residence time in the nasal cavity for better absorption.[76] By increasing the viscosity of the formulation, with polymers such as hypromellose or polyvinyl alcohol, it is possible to decrease mucociliary clearance.[77,78] Even though the cilia in the olfactory epithelium are non-motile, mucus clearance is still evident and most likely caused by gravity and continuous mucus production by the Bowman's gland. Charlton et al.[79] studied how some mucoadhesive agents can affect deposition and clearance to the olfactory region in humans. Their experiments compared the clearance of different low-molecular weight pectin and chitosan formulations in 12 human subjects administered as either liquid drops or atomized from a nasal spray device. The formulations contained fluorescein so that the deposition could be visually examined by endoscopy. Charlton et al. found no statistical difference in the clearance from the olfactory region between the formulations given as liquid drops. However, the residence time and deposition were significantly reduced after nasal spray administration, which was similar to the control buffer solution without a mucoadhesive agent. Formations with mucoadhesive agents are effective at extending residence times at the olfactory epithelium, but they are not the only factor for successful drug delivery in humans.

It has been shown that mucoadhesive and viscosity increasing agents are effective at increasing bioavailability from nasal formulations designed for systemic delivery.[80] To determine how the addition of a mucoadhesive agent can influence the absorption of drugs into the brain[81], Khan et al.[33] compared brain concentrations of buspirone after administration intravenously, intranasally as a solution and intranasally as a solution with 1% chitosan and 5% hydroxypropyl-β-cyclodextrin. They found that the AUC in the brain was 2.5-times higher for buspirone in the mucoadhesive formulation than in the intravenous solution, and 2-times as high as buspirone solution delivered intranasally. The excipients may have also contributed to the increase in brain concentration by increasing the permeability of the drug through the tight junctions of the nasal epithelium.[33]

Utilizing a novel formulation to increase nasal residence time and improve brain delivery, Bank et al.[59] compared brain concentrations after nasal delivery of testosterone in Noseafix® gel, which is comprised of castor oil, oleoyl polyoxyglycerides and amorphous silicon dioxide, to those measured after intravenous administration. They found significantly higher brain levels in all parts of the brain except the frontal cortex following intranasal administration. However, since the authors did not compare intranasal administration of testosterone without Noseafix®, no conclusion was stated about the effect the formulation had on increasing brain delivery. The increase in brain concentration may be attributed to intranasal administration alone.

Barakat et al.[34] studied nose-to-brain delivery of carbamazepine with the use of hypromellose and Carbopol 974P to form a gel to reduce clearance. They found the brain AUC-to-plasma AUC ratio was 4.31-times higher than from intravenous therapy. Carbamazepine has also been formulated in an in situ gelling formulation for direct nose-to-brain delivery.[35] The formulation consisted of carbamazepine, 18% Pluronic F-127 and 0.2% Carbopol 974P, which is a thermoreversible gel. A thermoreversible gel is liquid at room temperature, but quickly turns into a gel at body temperature, which provides an extended residence time in the nasal cavity.

When compared to intravenous administration of carbamazepine solution, Barakat et al. found that the intranasal formulation provided 100% systemic bioavailability. Even at early time points, they were unable to detect significantly higher brain levels in the intranasal group. Intranasal administration was performed on rats that were lying either on their side or in the supine position. Body position during intranasal administration plays a significant role on the deposition of formulation in the nasal cavity, targeting the respiratory region instead of the olfactory.

Other studies have reported on the effects that thermoreversible gels can have on direct nose-to-brain drug delivery. Ravi et al.[51] used poloxamer 407 and poloxamer 188 (1:1) with chitosan and Carbopol to develop a thermoreversible gel with rasagiline mesylate. Compared to a nasal solution of rasagiline in normal saline, the gel formulations exhibited significantly higher brain uptake. In a different formulation that also exhibited gelling at body temperature, Khan et al.[55] formed an in situ gel formulation comprised of chitosan and hypromellose to deliver ropinirole, and found that the AUC in the brain was 8.5-times higher compared to intravenous administration and nearly four times greater than ropinirole solution alone given intranasally.

Doxepin has been formed into a thermoreversible gel formulated with chitosan and glycerophosphate. Instead of accessing brain concentrations from homogenated brain tissue, the investigators assessed efficacy by a forced swim test, yet they saw no significant difference in duration of immobility when tested[38]. In situ gel preparations active in the presence of ions have also been developed and show the ability to form a gel in the presence of nasal secretions.[82] These studies, also shown in Table 1, describe that altering a formulation to increase the drug's residence time, allowing an increase in the time the formulation is in contact with the olfactory epithelium, generally lead to an increase in the amount of drug delivered to the brain.

iii. Polymeric Nanoparticles

A favorable formulation method for many routes of administration is the formation of nanosuspensions of drug encapsulated in polymeric carriers. These carriers may provide favorable characteristics to the drug like enhanced absorption, mucoadhesion and increased stability. Bhavna et al.[37] developed a nanosuspension formulation of donepezil, a cholinesterase inhibitor, for enhancing brain targeting to treat Alzheimer's disease. The nanosuspension is formed by crosslinking chitosan with tripolyphosphate to form nanoparticles that encapsulate donepezil. When tested in rats against donepezil suspension, the authors reported significantly higher AUC and maximum concentration in the brain after administration with the nanosuspension. The authors also observed significantly higher bioavailability with the nanosuspension so whether or not the increase in brain concentrations was due to direct nose-to-brain mechanisms is difficult to conclude.

In another paper, the authors tested chitosan nanoparticles loaded with bromocriptine.[32] In this study they compared bromocriptine-loaded nanoparticles given intranasally, bromocriptine-loaded nanoparticles given intravenously, and bromocriptine solution given intranasally. They found that bromocriptine-loaded nanoparticles given intranasally produced brain AUCs that were over two-fold greater than intravenous administration of the nanoparticles. Both nanoparticle formulations showed higher brain and plasma AUC values.

A novel polymeric carrier developed by Gao et al.[83] is comprised of wheat germ agglutinin conjugated to poly (ethylene glycol)-poly (lactic acid) (PEG-PLA) in an effort to increase absorption of nanoparticles to the brain. They used the nanoparticle carrier to encapsulate coumarin and found a two-fold increase in brain concentrations after intranasal administration compared to intranasal administration of unmodified PEG-PLA nanoparticles. In a later study, Gao et al. determined whether or not the nanoparticle carrier would be applicable to transport peptides to the brain.[84] They incorporated vasoactive intestinal peptide into the wheat germ agglutinin conjugated PEG-PLA nanoparticles.

When given intranasally, the authors reported 5.6-7.7 fold higher brain levels from the conjugated nanoparticles compared to vasoactive intestinal peptide given intranasally as a solution. Additionally, they also found higher brain levels from the conjugated nanoparticles compared to the peptide delivered in unmodified nanoparticles. The results from this study are displayed in FIG. 1, which shows the concentrations of vasoactive intestinal peptide measured in the olfactory bulb and olfactory tract (FIG. 1A), cerebrum (FIG. 1B) and cerebellum (FIG. 1C) after administration with the wheat germ agglutinin conjugated PEG-PLA nanoparticles, unmodified nanoparticles, or as a solution. Higher concentrations in the olfactory region (FIG. 1A) and the cerebellum (FIG. 1C) provide some evidence that the pathway for transport of the nanoparticles into the brain is along both the olfactory and trigeminal nerves. The novel carrier was assessed for toxicity issues during intranasal use by analyzing concentrations of surrogate markers, such as tumor necrosis factor alpha and wheat germ agglutinin specific antibodies, and concluded that the nanoparticles were a safe agent for use in intranasal therapy targeting the brain.[85] Seju et al.[47] used one of the most commonly used biodegradable polymers for nanoparticles, poly(lactic-co-glycolic acid) (PLGA).[47,86] The authors loaded olanzapine, an atypical antipsychotic, into the PLGA nanoparticles for intranasal delivery. The authors performed ex vivo permeation studies along with pharmacokinetic studies in rats and found the nanoparticles were slower to the diffuse the sheep nasal mucosa in the ex vivo study. However, in the pharmacokinetic study, they found 10.86 times higher drug accumulation in the brain after nanoparticle administration than olanzapine solution given intranasally, and 6.35 times higher than after drug solution given intravenously. Studies with polymeric nanoparticles are not yet conclusive on whether or not the particles are being absorbed into the brain or if the particles are adhering to the mucosal surface, followed by release of the drug. Gao et al.[83] discussed that the enhanced brain concentrations from the wheat germ agglutinin conjugated nanoparticles allowed binding with the nasal mucosal surface and then release of the drug. Bhavna et al. predicted that enhancements in brain delivery are also due to the mucoadhesive nature of chitosan. However, Fazil et al.[87] performed confocal laser scanning microscopy with rhodamine loaded chitosan nanoparticles and reported that intact particles were found in the brain. Seju et al.[47] predicted that olanzapine PLGA nanoparticles were transported as intact particles by endocytotic processes. Future studies are required to determine if the transport of the individual nanoparticle takes place for all nanoparticles, or if this is an advantage of a select few nanoparticle types. These studies, summarized in Table 1, show the promise that polymeric nanoparticle carriers can have on the delivery of both small molecules and peptides into the brain.

iv. Co-Administration Methods for Improved Delivery

The olfactory region receives its blood supply from small branches off the ophthalmic artery, while the respiratory region receives its blood supply from a large arterial branch from the maxillary artery. As a result, the respiratory region is highly innervated with blood vessels, making it an ideal target for systemic drug absorption.[14]. Often researchers target the olfactory region for nose-to-brain delivery, since this has fewer blood vessels contributing to plasma concentrations, while providing access to the olfactory nerve pathways. Dhuria et al.[88] studied the effect phenylephrine, a vasoconstrictor used for nasal decongestion, would have on increasing the brain to plasma AUC ratio. They tested brain concentrations after nasal administration of one of two neuropeptides, hypocretin-1 or dipeptide L-Tyr-D Arg. The use of the vasoconstrictor significantly decreased the amount of drug absorbed into the systemic circulation (as shown in FIG. 1); it also significantly increased the amount delivered to the olfactory bulb. However, this resulted in a decreased amount in the trigeminal nerve and about 50% decrease in whole brain concentrations of the neuropeptides. Use of a vasoconstrictor to modify drug absorption may be applicable for delivering some therapeutics to the brain depending on the risks of systemic exposure and location of the target for therapy. The CSF originates at the choroid plexus and eventually flows across the cribriform plate and into the nasal lymphatics.

Shingaki et al. tested the use of acetazolamide to increase brain concentrations of drugs delivered nasally.[31,42] Acetazolamide, a carbonic anhydrase inhibitor, functions to decrease the production of CSF. When rats were dosed with 5-FU with and without pre-administration of acetazolamide, Shingaki et al. found significantly higher CSF levels with the concomitant use of acetazolamide.[31] Similar studies with methotrexate produced similar results.[42] Co-administration with acetazolamide leads to a decrease in CSF secretion, which provides an increase in direct transport of drugs into the CSF.

v. Solubility and Permeability Enhancing

For drugs to take advantage of the extracellular mechanisms of drug transport they must cross the nasal epithelium. Since the trigeminal nerve ending is located in the lamina propria, it is necessary for drugs to cross the nasal epithelium to access this pathway. In targeting drug delivery to the system circulation, many agents have been used to increase the permeation of drugs across the epithelium.[89-94] Agents used to increase the permeability across a membrane are referred to as permeation enhancers. Since the nasal epithelial layer is connected by tight junctions, permeation enhancers that open tight junctions may be useful in improving drug delivery to the brain. Some studies have used borneol[95], chitosan and cyclodextrins[33,40] to help improve direct nose-to-brain drug transport. Other methods to increase delivery of drugs to the brain use lipid components like microemulsions. Microemulsions can increase the concentration of hydrophobic drugs to be delivered, as well as increase the permeability across membranes.[96] Jogani et al.[58] developed a microemulsion formulation of tacrine for delivery to the brain.

Firstly, they prepared a solution of tacrine in propylene glycol and water and compared its brain delivery after intranasal and intravenous administration. They found that the direct transport efficiency (DTE) was 207.23.[57] DTE is a comparison of ratios of the AUC in the brain compared to plasma after intranasal administration compared to intravenous administration, and is described by the following equation:

$$\% \ DTE = \frac{[AUC_{brain}/AUC_{blood} i.n.]}{[AUC_{brain} = AUC_{blood} i.v.]} \times 100\%$$

Values greater than one, indicate that a higher brain/plasma ratio is obtained from intranasal administration as compared to intravenous administration. Jogani et al. then incorporated tacrine into a microemulsion formulation and a mucoadhesive microemulsion using the mucoadhesive agent Carbopol 934P.

The authors then compared brain delivery to mice from tacrine solution given intranasally and intravenously to tacrine microemulsion and tacrine mucoadhesive microemulsion given intranasally. The tacrine mucoadhesive microemulsion showed the highest DTE of 295.87%, followed by the tacrine microemulsion (DTE 242.82%) and then tacrine solution (DTE 207.23%). Many different investigators have looked at the effects microemulsion and nanoemulsions with and without the use of mucoadhesive agents can have on direct nose-to-brain delivery (Table 1).[41,45,46,48,56,97,98] For instance, Patel et al. 49 studied the pharmacokinetics from a paliperidone microemulsion formulation intended for delivery to the brain. Instead of Carbopol 934P, Patel et al. used polycarbophil as a mucoadhesive agent in the formulation.

When given in rats, the mucoadhesive microemulsion formulation gave the highest DTE, 320.69%, which was 1.74-fold higher than paliperidone given intranasally as a solution. Additionally, the intranasal mucoadhesive microemulsion produced brain AUCs that were 2.43 times higher than after intravenous administration of the microemulsion. One study used an in situ gelling agent to increase the residence time in the nasal cavity after the microemulsion is administered. Wang et al.[36] developed a microemulsion using deacetylated gellan gum for ion activated in situ gelling. When testing with curcumin, they found the DTE to be 6.50 and a brain AUC three times that after curcumin injection.

Curcumin has also been used to study the effects of an optimized mucoadhesive nanoemulsion ex vivo permeation through sheep nasal mucosal as well as in vitro toxicity studies. The mucoadhesive agent used with the nanoemulsion was chitosan. The investigators found that their nanoemulsion did not cause noticeable toxicity issues and increased curcumin permeation across the nasal mucosal.[99]

Figure 2:
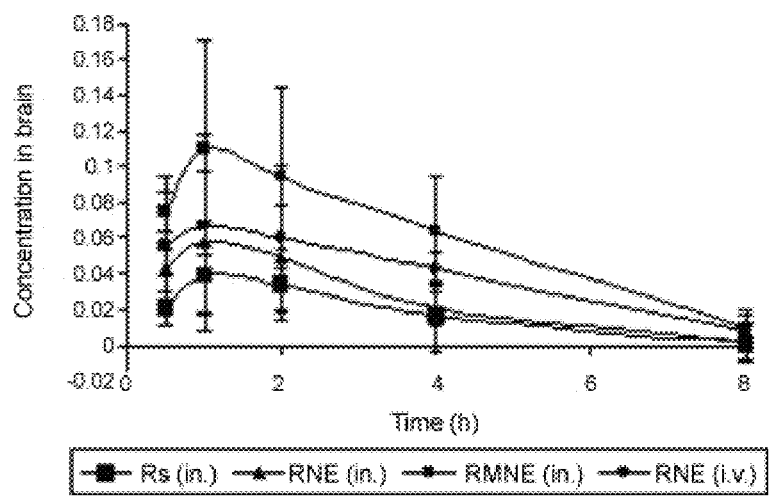
FIG. 2 illustrates a graph of brain risperidone concentration vs. time following administration. Brain risperidone concentration vs. time following administration with risperidone solution (i.n.), risperidone nanoemulsion (i.n.), mucoadhesive risperidone (i.n.) and risperidone nanoemulsion (i.v.). (Reprinted with permission from Kumar et al., 2008).

Risperidone has also been formulated into a mucoadhesive nanoemulsion.[53] The mucoadhesive agent added to the nanoemulsion was 0.5% chitosan. The DTE was found to be 476 when tested in rats. The intravenous control in the experiment was risperidone nanoemulsion, which shows higher brain intake was not due to the nanoemulsion alone, but also contributed to by direct nose-to-brain pathways, as shown in FIG. 2. The locomotor activity was significantly reduced in mice when treated with any of the tested formulations of risperidone. There was a significant reduction in activity from the risperidone nanoemulsion and mucoadhesive nanoemulsion given intranasally compared to the risperidone nanoemulsion given intravenously.

Risperidone has also been formulated as solid lipid nanoparticles for nose-to-brain delivery.[54] Solid lipid nanoparticles reportedly provide many advantages over solution and drug suspension dosage forms. They can entrap the drug, giving the ability to control release and to improve stability. Additionally, they possess many of the advantages of microemulsion and nanoemulsions. Solid lipid nanoparticles have recently received a lot of attention in delivery therapeutics using direct nose-to-brain drug delivery, as seen in table 1.[54,61,100,101] Patel et al. 54 entrapped risperidone into solid lipid nanoparticles (SLNs) and gave them intranasally and intravenously.

Risperidone solution was also given intravenously. It was shown that the SLNs given intranasally produced a brain to plasma AUC ratio fivefold higher than the SLN formulation given intravenously and tenfold higher than the risperidone solution given intravenously. The brain AUC values after risperidone SLNs were administered intranasally and intravenously were similar; however, the plasma AUC after intranasal administration was lower. In theory, this would allow for equal efficacy while reducing systemic side effects by lowering the plasma concentration. Similarly, Alam et al.[39] studied the effects that a lipid nanocarrier of duloxetine would have on brain delivery. They found the lipid nanocarrier formulations provided about eight times higher brain concentrations when compared to intravenous administration of duloxetine solution and a DTE of 757.14%.

Intranasal administration of duloxetine solution produced a DTE of 287.34%, showing that the lipid nanocarrier formulation was able to significantly influence the amount delivered to the brain. Many of the above-mentioned studies took place using psychiatric medications, but another area for therapeutic improvement using this pathway is the treatment of migraines. Jain et al.[62] produced a micellar formulation of zolmitriptan, a medication indicated for migraine treatment. The goal of the formulation would be to maintain the rapid onset of action provided by intranasal zolmitriptan while improving its efficacy and duration of action. They found that after administering the micellar formulation, there was about fivefold higher brain concentrations in rats as soon as 30 minutes after administration, and the formulation continued to show significantly higher brain concentrations up to 120 minutes. Further clinical study is required to see how this could affect treatment of migraines, however it has been observed that it is possible to increase zolmitriptan brain uptake in this manner.

EXAMPLES

Example 1

Figures 16, 17, 18:
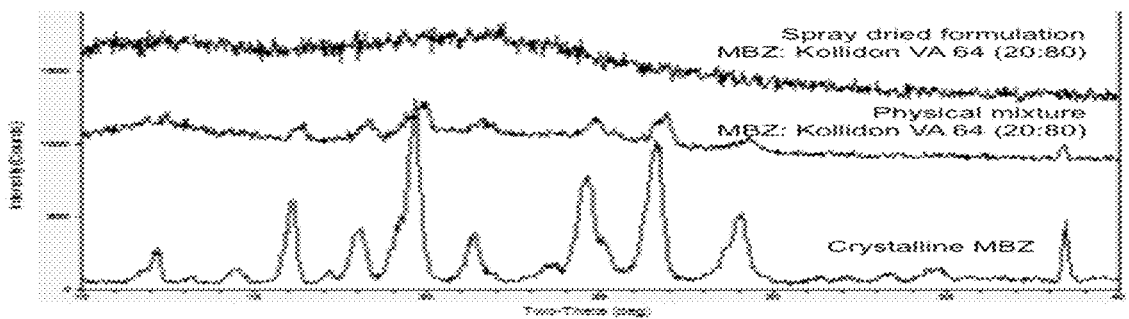
FIG. 16 illustrates the powder X-ray diffraction spectra for the spray dried mebendazole and Kollidon VA 64® formulation, a physical mixture of mebendazole and Kollidon VA 64®, and crystalline mebendazole (from top to bottom).
FIG. 17 illustrates a formulation table for a fluorescein-labeled foam formulation for delivery to the olfactory region of a human.
FIG. 18 illustrates an illustrative example of an anatomically correct nasal cast developed based on CT-scans of patients (left) followed by 3D printing (right). The casts were segmented into five different sections (A=anterior, U=upper turbinate region, M=middle turbinate region, L=lower turbinate region, N=nasopharynx) to quantitate the deposition pattern within the nasal cavity.

The nasal implant requires solutions which can achieve sufficient concentrations of the active therapeutic agents to delivery an effective amount to the appropriate nasal surfaces. To achieve a sufficient concentration, the therapeutic agents were formulated as a solid dispersion powder. To form the solution of the solid dispersion components, mebendazole and Kollidon VA 64® were dissolved at a 1:4 ratio in 0.62% HCl:49.7% methanol: 49.7% tetrahydrofuran. This solution was spray dried in a Buchi B-290 at inlet temperature 100° C., Pump 15% and Qflow 40 mm. The resulting solid dispersion was amorphous according to PXRD spectra (FIG. 16) and exhibited supersaturation upon dissolution in deionized water (FIG. 15). As a comparison, FIG. 16 shows the PXRD spectra of a physical mixture as well as crystalline mebendazole. The amorphous nature as well as the supersaturated characteristic of the solution indicated favorable solution characteristic for the use in an intranasal delivery device.

Example 2

The following process was used to produce a solid dispersion of mebendazole.

TABLE 2

| | Parts by weight | | |
|---|---|---|---|
| No. | Mebendazole | Povidone K30 | Kollidon VA 64 ® |
| 1 | 1 | 1 | 0 |
| 2 | 1 | 2 | 0 |
| 3 | 1 | 3 | 0 |
| 4 | 1 | 0 | 1 |
| 5 | 1 | 0 | 2 |
| 6 | 1 | 0 | 3 |

Solutions of the solid dispersion components were prepared by dissolving the component in 20% formic acid: 80% acetone. The resulting solutions was spray dried in a Buchi B-290 at inlet temperature of 100° C., pump 15%, Aspirator 100% and a Qflow of 55 mm. The resulting solid dispersion were analysed by PXRD for detection of crystallinity. Crystallinity was observed in all preparations except No. 3 and No. 6.

Example 3

Figure 19:
FIG. 19 illustrates deposition results for the formulation of FIG. 17.

In order to determine the delivery location of the preparation using the intranasal delivery device, a foam formulation was prepared using fluorescein. The composition components and amounts are shown in FIG. 17. All of the components except HFA 227 were added into a canister and a continuous spray valve was crimped on followed by addition of HFA 227 by pressure filling. Actuation of foam was performed with a prototype device as disclosed herein, with an actuator adapted from an 18 gauge syringe for directing foam deposition. In order to quantitate the drug deposition in different regions of the nasal casts, they were each divided into five separate parts based on anatomy, as shown in FIG. 18. As shown in FIG. 19, the percent deposited in the upper region was 27.9 percent, compared to 9.0 percent for the anterior region, 29.5 percent for the middle region, 33.6 percent for the lower region and 0 percent for the nasopharynx region.

Example 4

Figure 20:
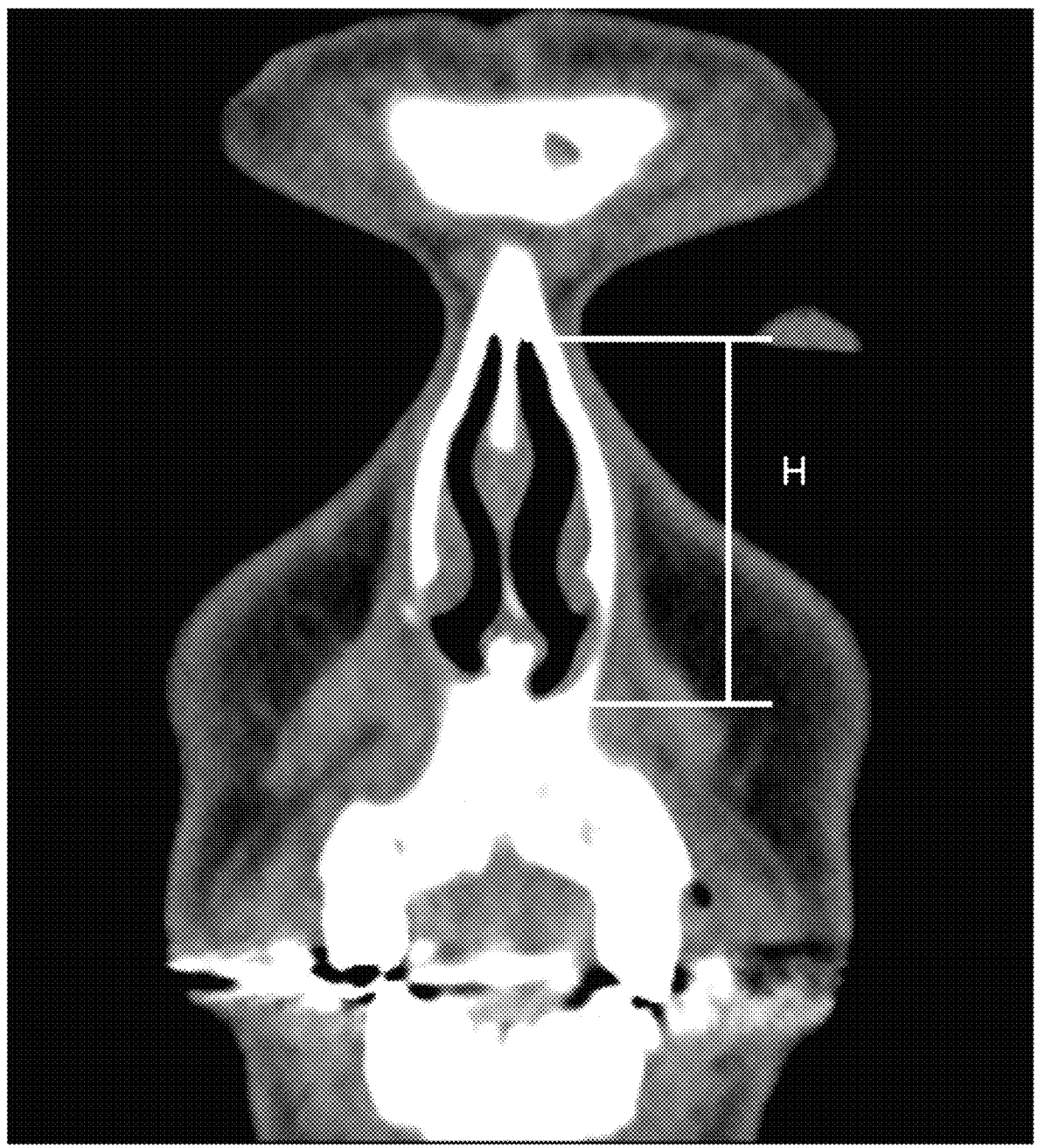
FIG. 20 illustrates an example of nasal geometry measurements to compare nasal casts.

Nasal replica casts that anatomically represent the nasal cavities of individuals were fabricated to study the regional deposition of compositions within the nasal cavity. CT-scans of individuals were uploaded into 3D Slicer software (http://www.slicer.org). FIG. 4 shows an example of the CT-scan of an individual before segmentation of the nasal cavity. Threshold effects within the editor module of the software were used to segment the region of the nasal cavity. Manual edits were used to remove the sinuses from the nasal cavity segment. The model feature of the editor module was used to create a model of the segmented nasal cavity from the CT-scan in a format that could be 3D-printed. The 3D model was printed by W. M. Keck Center for 3D innovation (El Paso, USA) using a Viper™ HA SLA® system (3D Systems Corp., Valencia, USA) with build layer thickness of 0.004 inches and resolution of 0.010 inches using Somos® Watershed XC 11122 (DSM Somos®, Elgin, USA) as the material. The age, gender and basic geometric parameters are provided in Table 3. The measurements used to depict the geometric parameters of the nasal cast replicas is presented in FIG. 20.

TABLE 3

| Cast | Age | Gender | $Area_{min}$ $(mm^2)$ | $Length_{n-t}$ $(mm)$ |
|---|---|---|---|---|
| C1 | 12 | Female | 258.344 | 75.884 |
| C2 | 7 | Female | 113.969 | 59.159 |
| C3 | 7 | Female | 217.201 | 59.791 |
| C4 | 9 | Female | 173.471 | 63.609 |
| C5 | 14 | Female | 299.155 | 68.990 |
| C6 | 48 | Male | 249.173 | 88.000 |
| C7 | 33 | Male | 279.347 | 86.680 |
| C8 | 44 | Female | 218.720 | 80.730 |
| C9 | 48 | Male | 249.300 | 86.000 |
| C10 | 31 | Female | 213.241 | 78.207 |
| | Pediatric (n = 5) | Adult (n = 5) | | |
| Age (yrs.) | 9.8 (3.1) | 40.8 (8.2) | | |

TABLE 3-continued

| Cast | Age | Gender | $Area_{min}$ $(mm^2)$ | $Length_{n-t}$ $(mm)$ |
|---|---|---|---|---|
| $Area_{min}$ $(mm^2)$ | 212.428 (72.223) | 241.956 (26.780) | | |
| $Length_{n-t}$ | 65.487 (7.007) | 83.923 (4.225) | | |

$Area_{min}$ = minimum coronal cross-section area; $Length_{n-t}$ = length from nostrils to the end of the turbinates
Averages presented as mean (standard deviation)

Example 5

Deposition studies, in nasal replica cast C3 from Example 4, were used to compare the effect of administration angles on deposition to the to the upper region of the nasal cavity. The device used in this example was a prototype device resembling FIG. 11. The device consisted of a propellant canister connected to a dosing chamber modified from a 2 mL microcentrifuge tube which was further connected to the top 1.5 inches of a 5000 mL pipette tip (Eppendorf, Germany) with an anatomically-positioning insert. HFA 134a was used as propellant to propel the powder from the device. The anatomically-positioning insert was developed by creating a negative mold of the nostrils of the individuals from the 3D-printed models using Copyflex® (MakeYourOwn-Molds, Cincinnati, USA) around the device fixed at a specific position.

Deposition in each region of the nasal cavity was performed using a powder comprised of 5% (w/w) fluorescein in InhaLac® 70 (MEGGLE, Germany). 5 mg of the powder was loaded into the device, which was dispensed by actuation of the Metered Dose Inhaler canister fitted with a valve set to deliver 100 μL of propellant. The insertion depth of the device was set at 10 mm. The deposition in each region was measured by washing each region of the nasal cast with 5 mL of 3% w/v sodium hydroxide aqueous solution and measuring UV absorbance at 494 nm for each cast. FIG. 6 illustrates the individual regions of the nasal cast.

The deposition study results are shown in Table 4. The sagittal angle is presented with respect to the base of the nasal cavity. The coronal angle is depicted as being positive towards the septum. The coronal angle and sagittal angles are depicted with respect to the nasal cavity in FIG. 8 as A and B respectively.

Changes in the angle of administration created differences in the deposition to the upper region of the nasal cavity. As differences in the administration angle affect the deposition pattern of the powder, controlling the angle of administration affects the deposition pattern. As evident, by controlling the sagittal and coronal angles for nasal replica cast C3, the anatomical positioning is important to optimize its upper region deposition, and therefore the upper region deposition must be optimized for individualized administration.

TABLE 4

| Sagittal Angle (degrees) | Coronal Angle (degrees) | Upper region deposition (% deposited) |
|---|---|---|
| 62.0 | 34.8 | 6.7% |
| 65.0 | 7.6 | 13.6% |
| 60.0 | 1.0 | 15.6% |

Example 6

The anatomical positioning device can be modeled based on the CT scan of the individuals. In this example, the device used for deposition experiments was the same as that described in Example 2 except that the anatomically-positioning insert was developed by 3D-printing the negative model of the nostril with a hole placed near the middle of the insert, which allows the device tip to be inserted at a specified depth and angle into the nostril of the cast.

Deposition in each region of the nasal cavity (C3 from Table 1, Example 1)) was performed with a powder comprised of 5% (w/w) fluorescein in InhaLac® 70 (MEGGLE, Germany). 5 mg of the powder was loaded into the device which was activated by actuation of the Metered Dose Inhaler canister fitted with a valve set to deliver 100 μL of liquid propellant. The insertion depth of the device was set at 10 mm. The sagittal angle with respect to the base of the nasal cast was degrees and the coronal angle with respect to the septum was 6.6 degrees. Deposition in each region was quantified using the method described in Example 2. The percentage of deposited fluorescein measured in the upper region compared to the entire cast was 22.0% with a standard deviation of 3.6%. As evident, by controlling the sagittal and coronal angle for nasal replica cast C3, the anatomical positioning is important to obtain reproducible upper region deposition.

Example 7

Individualized administration parameters can be obtained by use of the CT-scan images. The angles for administration to target the upper region of the nasal cavity were determined based on factors found in the specific CT-scan for each individual. The angles in the coronal and sagittal planes were determined based on the positioning of two points. Point 1 was placed in the center of the nostril at the beginning of the nasal cavity. Point 2 was placed in the coronal plane CT slice that was located at 0.3 multiplied by the length (L) of the nasal cavity (FIG. 21), zero defined at the anterior portion of the cavity comprising the nostril region. Point 2 was placed at 0.7 multiplied by the height (H) of the nasal cavity at the previously determined coronal place slice (FIG. 22). The coronal and sagittal angles were calculated based on equation 1 and equation 2, respectively. Where x, y, and z points correspond to their coordinates in the Cartesian plane found in 3D Slicer software's view of the CT-scans. Table 5 presents the angles of administration determined for the left nostril of each individual. The angles determined from this example are referred to as the CT-scan based angle.

$$\text{Coronal angle} = \tan^{-1} \frac{y_2 - y_1}{(x_2 - x_1)}. \quad \text{Equation 1}$$

$$\text{Sagittal angle} = \tan^{-1} \frac{y_2 - y_1}{(z_2 - z_1)}. \quad \text{Equation 2}$$

TABLE 5

| Individual | Sagittal Angle (degrees) | Coronal Angle (degrees) |
|---|---|---|
| 1 | 53.3 | −1.9 |
| 2 | 61.1 | 7.2 |
| 3 | 55.9 | 9.7 |
| 4 | 60.6 | 5.2 |
| 5 | 64.3 | 4.3 |
| 6 | 60.4 | 5.8 |
| 7 | 58.5 | 1.2 |

TABLE 5-continued

| Individual | Sagittal Angle (degrees) | Coronal Angle (degrees) |
|---|---|---|
| 8 | 61.0 | 2.5 |
| 9 | 60.0 | 1.0 |

Example 8

Individualized administration parameters can be obtained by use of the three-dimensional model of the nasal cavity. The angles for administration to target the upper region of the nasal cavity were determined based on the relative force of airflow that passed to the upper region of the nasal cavity. The upper region of the nasal cavity was removed from the nasal cast, which was otherwise assembled and placed over an analytical balance (Mettler Toledo, Columbus, USA) with the nostril opening facing away from the balance plate. (FIG. 23) Airflow was produced using a jet nebulizer compressor (Pari, Midlothian, VA) and directed through a nozzle developed with a 5 mL pipette tip (Eppendorf, Germany). The nozzle was placed in to a nostril of the nasal cast and airflow was allowed to flow through the cast and impact on the balance. The relative force produced by the airflow was logged using the serial port on the analytical balance.

To obtain the angle in which the nozzle was placed into the nasal casts over time, two cameras were set up on adjacent sides of the nasal cast. One camera captured the sagittal plane of the nasal cast, providing the sagittal angle of the nozzle, while the other captured the coronal plane of the nasal cast, providing the coronal angle of the nozzle. The picture frames corresponding to the time at which the relative force of the airflow was at its maximum were used to measure the sagittal and coronal angles using ImageJ angle tool. Table 6 depicts the administration angles found using this method for the left nostril of each individual. The angles used in this method are henceforth referred to as the airflow based angle.

TABLE 6

| Individual | Sagittal Angle (degrees) | Coronal Angle (degrees) |
|---|---|---|
| 1 | 46.0 | −5.2 |
| 2 | 67.1 | 23.1 |
| 3 | 55.8 | 14.4 |
| 4 | 56.0 | 4.3 |
| 5 | 67.5 | 16.8 |
| 6 | 50.3 | −3.8 |
| 7 | 60.0 | 9.2 |
| 8 | 71.5 | 6.7 |
| 9 | 60.7 | 6.6 |

Example 9

The deposition to the upper region of the nasal cavities described in Example 1 was produced with the device described in Example 2, with anatomical—positioning inserts created for each individual controlling for the CT-scan based angles presented in Table 3. Deposition experiments were performed in the left nostril of each cast. Deposition in each region of the nasal cavity was performed with a powder comprised of 5% (w/w) fluorescein in InhaLac® 70 (MEGGLE, Germany). 5 mg of the powder was loaded into the device which was activated by actuation of the Metered Dose Inhaler canister fitted with a valve set to delivery 100 µL. The insertion depth of the device was set at 10 mm. The percentage of deposited fluorescein found in the upper region for each cast is depicted in Table 7 as determined based on the quantification method presented in Example 2.

TABLE 7

| Cast of individual described in Table 3 | Upper region deposition (% of detected) |
|---|---|
| 1 | 35.5% |
| 2 | 9.1% |
| 3 | 3.2% |
| 4 | 35.0% |
| 5 | 7.1% |
| 6 | 3.1% |
| 7 | 54.2% |
| 8 | 41.1% |
| 9 | 15.8% |

Example 10

The deposition to the upper region of the nasal cavities described in Example 1 was produced with the device described in Example 2, with anatomical—positioning inserts created for each individual controlling for the airflow based angles presented in Table 3. Deposition experiments were performed in the left nostril of each cast. Deposition in each region of the nasal cavity was performed with a powder comprised of 5% (w/w) fluorescein in InhaLac® 70 (MEGGLE, Germany). 5 mg of the powder was loaded into the device which was activated by actuation of the Metered Dose Inhaler canister fitted with a valve set to delivery 100 µL. The insertion depth of the device was set at 10 mm. The percentage of deposited fluorescein found in the upper region for each cast is depicted in Table 8 as determined based on the quantification method presented in Example 2.

TABLE 8

| Cast of individual described in Table 3 | Upper region deposition (% of detected) |
|---|---|
| 1 | 11.9% |
| 2 | 15.8% |
| 3 | 10.7% |
| 4 | 50.3% |
| 5 | 16.7% |
| 6 | 5.3% |
| 7 | 48.8% |
| 8 | 26.7% |
| 9 | 12.4% |

Example 11

The deposition to the upper region of the nasal cavities described in Example 1 was produced with the device described in Example 2, with anatomical—positioning inserts created for each individual controlling the administration angles to a sagittal angle of 55.0 degrees and coronal angle of 5.0 degrees for all casts. Deposition experiments were performed in the left nostril of each cast. Deposition in each region of the nasal cavity (C3 from Example 1)) was performed with a powder comprised of 5% (w/w) fluorescein in InhaLac® 70 (MEGGLE, Germany). 5 mg of the powder was loaded into the device, which was activated by actuation of the Metered Dose Inhaler canister fitted with a valve set to deliver 100 µL. The insertion depth of the device was set at 10 mm. The percentage of deposited fluorescein found in the upper region for each cast is depicted in Table 9 as determined based on the quantification method presented in Example 2. The angle used in this test is henceforth referred to as the common use angle.

TABLE 9

| Cast | Upper region deposition (% of detected) |
|---|---|
| 1 | 46.6% |
| 2 | 8.1% |
| 3 | 18.4% |
| 4 | 33.4% |
| 5 | 18.4% |
| 6 | 2.9% |
| 7 | 41.3% |
| 8 | 36.7% |
| 9 | 2.0% |

Example 12

The individualized administration to a person can be further optimized by testing the deposition to a particular region using the parameters determined by various methods. The selection for the patient-specific angle for targeting to upper region of the nasal cast is determined based on the relative improvement in deposition using the CT-Scan based angles and the airflow based angles compared to all casts using the common use angle is compared in TABLE 10. The percentage of deposited fluorescein to the upper region of the cast for CT-scan based angle, airflow based angles and common use angle is divided by the results found for each cast using the common use angle to compare the relative improvement in deposition to this region. The olfactory targeting patient-specific angle for targeting the upper region of the nasal cavity is taken as the administration angle method presenting the highest value for each patient.

TABLE 10

| | Relative deposition compared to common use angle | | |
|---|---|---|---|
| Cast | CT-scan based angle | Airflow based angle | Common use angle |
| 1 | 0.25 | 0.76 | 1.00 |
| 2 | 1.95 | 1.12 | 1.00 |
| 3 | 0.58 | 0.18 | 1.00 |
| 4 | 1.51 | 1.05 | 1.00 |
| 5 | 0.91 | 0.38 | 1.00 |
| 6 | 1.85 | 1.09 | 1.00 |
| 7 | 1.18 | 1.31 | 1.00 |
| 8 | 0.73 | 1.12 | 1.00 |
| 9 | 6.17 | 7.86 | 1.00 |

Example 13

The use of patient-specific administration angles for targeting the upper region is compared to all casts using the common use angle. Table 11 depicts the relative deposition using the olfactory targeting patient-specific angle compared to the common use angle for each individual. There was an average improvement of 2.07-fold using the olfactory targeting patient-specific angle compared to the common use angle for targeting the upper region of the nasal cast. By individualizing the administration to each individual, the upper region targeting was improved compared to all individuals using the same parameters.

TABLE 11

| Cast | Relative deposition compared to common use angle |
|---|---|
| 1 | 1.00 |
| 2 | 1.95 |
| 3 | 1.00 |
| 4 | 1.51 |
| 5 | 1.00 |
| 6 | 1.85 |
| 7 | 1.31 |
| 8 | 1.12 |
| 9 | 7.86 |
| Average | 2.07 |

Example 14

In this example, the device used was a metered dose pump spray device, VP7 (Aptar Pharma, Le Vaudreuil, France). Cromolyn sodium nasal solution, USP was formulated with the addition of hypromellose E4M at 0.8% w/v. The nasal spray was actuated into the nasal casts described in Example 1. To evaluate the effect of patient-specific angles, which are designed for turbinate drug delivery, a central-composite design of experiments was conducted. The output variable for optimization was percentage of deposited cromolyn sodium in the turbinate region. The inputs studied were the coronal plane and sagittal plane angles of administration of the nasal spray device. Table 12 depicts the coronal and sagittal angle ranges used in the design of experiments for each cast. The central composite design was developed with an axial value that allowed the design to be rotatable and contained three central points. The statistical design of experiments were generated and analyzed by standard least squares regression using JMP® Pro 13 (SAS Institute, Inc., Cary, USA). The predicted angle for each cast that maximized the turbinate deposition efficiency was tested, and it was considered the patient-specific angle. The predicted optimal angles for each cast are presented in Table 13.

To quantitate cromolyn sodium deposition in each region of the nasal cast, the cast was dissembled and each part of the cast was washed with 5 mL of deionized water. The concentration of cromolyn sodium in the wash fluid of each part was assessed by UV absorbance at 326 nm.

The administration angles of the nasal spray device were controlled by mechanically fixing the position of the MightyRunt actuator with the use of a rotatable vice.

TABLE 12

| Cast | Coronal angle range (degrees) | Sagittal angle range (degrees) |
|---|---|---|
| C1 | 0-20 | 30-45 |
| C2 | 0-20 | 30-45 |
| C3 | 0-20 | 35-50 |
| C4 | 0-20 | 35-50 |
| C5 | 0-20 | 30-45 |
| C6 | 0-20 | 30-45 |
| C7 | 0-20 | 35-50 |
| C8 | 0-20 | 35-50 |
| C9 | 0-20 | 35-50 |
| C10 | 0-20 | 35-50 |

TABLE 13

| | Patient- Specific Angle (degrees) | |
|---|---|---|
| Cast | Coronal Angle (degrees) | Sagittal Angle (degrees) |
| C1 | 20.0 | 30.0 |
| C2 | 20.0 | 34.4 |
| C3 | 20.0 | 35.0 |
| C4 | 20.0 | 35.0 |
| C5 | 15.7 | 30.0 |
| C6 | 18.5 | 35.3 |
| C7 | 14.7 | 35.0 |
| C8 | 0.0 | 35.0 |
| C9 | 10.3 | 35.0 |
| C10 | 14.0 | 35.0 |

Example 15

To optimize the percentage of deposited cromolyn sodium in the turbinate region, the determined patient-specific angles from Example 7 were compared with the percent drug deposited when all casts used an administration angle of 30 degrees from horizontal in the sagittal plane and zero degrees from the septum in the coronal plane as a comparative example. The results of the turbinate deposition efficiency are presented in Table 14. As shown in FIG. 24, the use of the patient-specific angle significantly increased the turbinate deposition efficiency compared to that found for all subjects using an administration angle of 30°, around 90% compared to about 73%. When the administration angle was maintained in all the replicas, we found turbinate deposition increased with decreases in the administration angle. Deposition to the upper regions of the replica was poor with any formulation or administration angle tested. Personalized delivery using patient-specific angles increases the turbinate targeting of the tested formulation compared to each cast using the comparative administration angle.

TABLE 14

| | % deposited cromolyn sodium in turbinate region | |
|---|---|---|
| Cast | Patient-specific angle (degrees) | 30 degrees/ 0 degrees (degrees) |
| C1 | 97.1% | 73.0% |
| C2 | 93.8% | 76.8% |
| C3 | 97.8% | 85.8% |
| C4 | 97.0% | 69.9% |
| C5 | 95.8% | 81.7% |
| C6 | 86.9% | 87.9% |
| C7 | 75.7% | 46.4% |
| C8 | 81.5% | 62.9% |
| C9 | 81.4% | 65.5% |
| C10 | 97.7% | 79.5% |
| Average (standard deviation) | 90.5% (8.3%) | 72.9% (12.4%) |

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
1. Sakr, A. & Alanazi, F. in Remington: The Science and Practice of Pharmacy (eds. Allen, L. V., Jr., Ph D., Adejare, A., Ph D., Desselle, S. P., Ph D. & Felton, L. A., Ph D.) (Pharmaceutical Press, 2012).
2. Lockhead, J. & Thorne, R. G. in Drug Delivery to the Brain: Physiological Concepts, Methodologies and Approaches (Springer Science & Business Media, 2013).
3. Thorne, R. G., Emory, C. R., Ala, T. A. & Frey II, W. H. Quantitative analysis of the olfactory pathway for drug delivery to the brain. Brain Res. 692, 278-282 (1995).
4. Frey, W. H. et al. Delivery of 125I-NGF to the Brain via the Olfactory Route. Drug Deliv. 4, 87-92 (1997).
5. Wu, H., Hu, K. & Jiang, X. From nose to brain: understanding transport capacity and transport rate of drugs. Expert Opin. Drug Deliv. 5, 1159-1168 (2008).
6. Striepens, N. et al. Elevated cerebrospinal fluid and blood concentrations of oxytocin following its intranasal administration in humans. Sci. Rep. 3, (2013).
7. Craft S, Baker L D, Montine T J & et al. Intranasal insulin therapy for alzheimer disease and amnestic mild cognitive impairment: A pilot clinical trial. Arch. Neurol. 69, 29-38 (2012).
8. Djupesland, P. G. & Skretting, A. Nasal deposition and clearance in man: comparison of a bidirectional powder device and a traditional liquid spray pump. J. Aerosol Med. Pulm. Drug Deliv. 25, 280-289 (2012).
9. Kublik, H. & Vidgren, M. T. Nasal delivery systems and their effect on deposition and absorption. Adv. Drug Deliv. Rev. 29, 157-177 (1998).
10. Hardy, J. G., Lee, S. W. & Wilson, C. G. Intranasal drug delivery by spray and drops. J. Pharm. Pharmacol. 37, 294-297 (1985).
11. Giroux, M. Particle dispersion device for nasal delivery. (2007).
12. Thomas, C. & Ahsan, F. in Pharmaceutical Manufacturing Handbook: Production and Processes (ed. Gad, S. C.) 591-650 (Wiley-Interscience, 2008).
13. Illum, L. Nasal drug delivery—possibilities, problems and solutions. J. Controlled Release 87, 187-198 (2003).
14. Dhuria, S. V., Hanson, L. R. & Frey, W. H. Intranasal delivery to the central nervous system: Mechanisms and experimental considerations. J. Pharm. Sci. 99, 1654-1673 (2010).
15. Pardeshi, C. V. & Belgamwar, V. S. Direct nose to brain drug delivery via integrated nerve pathways bypassing the blood-brain barrier: an excellent platform for brain targeting. Expert Opin. Drug Deliv. 10, 957-972 (2013).
16. Clerico, D., To, W. & Lanza, D. in Handbook of Olfaction and Gustation 1-16 (CRC Press, 2003).
17. Mygind, N. & Dahl, R. Anatomy, physiology and function of the nasal cavities in health and disease. Adv. Drug Deliv. Rev. 29, 3-12 (1998).
18. Ruigrok, M. J. R. & de Lange, E. C. M. Emerging Insights for Translational Pharmacokinetic and Pharmacokinetic-Pharmacodynamic Studies: Towards Prediction of Nose-to-Brain Transport in Humans. AAPS J. (2015). doi:10.1208/s12248-015-9724-x
19. Lochhead, J. J. & Thorne, R. G. Intranasal delivery of biologics to the central nervous system. Adv. Drug Deliv. Rev. 64, 614-628 (2012).
20. Verreck, G. et al. Characterization of solid dispersions of itraconazole and hydroxypropylmethylcellulose prepared by melt extrusion—part I. Int. J. Pharm. 251, 165-174 (2003).
21. Weuts, I. et al. Physicochemical properties of the amorphous drug, cast films, and spray dried powders to predict formulation probability of success for solid dispersions: Etravirine. J. Pharm. Sci. 100, 260-274 (2011).
22. DiNunzio, J. C. et al. Fusion production of solid dispersions containing a heat-sensitive active ingredient by hot melt extrusion and Kinetisol® dispersing. Eur. J. Pharm. Biopharm. 74, 340-351 (2010).
23. Betageri, G. V. & MakarlaA, K. R. Enhancement of dissolution of glyburide by solid dispersion and lyophilization techniques. Int. J. Pharm. 126, 155-160 (1995).
24. Zhang, M. et al. Formulation and delivery of improved amorphous fenofibrate solid dispersions prepared by thin film freezing. Eur. J. Pharm. Biopharm. 82, 534-544 (2012).
25. Shah, N. et al. Improved human bioavailability of vemurafenib, a practically insoluble drug, using an amorphous polymer-stabilized solid dispersion prepared by a solvent-controlled coprecipitation process. J. Pharm. Sci. 102, 967-981 (2013).
26. Won, D.-H., Kim, M.-S., Lee, S., Park, J.-S. & Hwang, S.-J. Improved physicochemical characteristics of felodipine solid dispersion particles by supercritical antisolvent precipitation process. Int. J. Pharm. 301, 199-208 (2005).
27. Arzhavitina, A. & Steckel, H. Foams for pharmaceutical and cosmetic application. Int. J. Pharm. 394, 1-17 (2010).
28. Zhao, Y., Brown, M. B. & Jones, S. A. Engineering novel topical foams using hydrofluroalkane emulsions stabilised with pluronic surfactants. Eur. J. Pharm. Sci. 37, 370-377 (2009).
29. Zhao, Y., Brown, M. B. & Jones, S. A. Pharmaceutical foams: are they the answer to the dilemma of topical nanoparticles? Nanomedicine Nanotechnol. Biol. Med. 6, 227-236 (2010).
30. Zhao, Y., Moddaresi, M., Jones, S. A. & Brown, M. B. A dynamic topical hydrofluoroalkane foam to induce nanoparticle modification and drug release in situ. Eur. J. Pharm. Biopharm. 72, 521-528 (2009).
31. Shingaki, T. et al. The transnasal delivery of 5-fluorouracil to the rat brain is enhanced by acetazolamide (the inhibitor of the secretion of cerebrospinal fluid). Int. J. Pharm. 377, 85-91 (2009).
32. Md, S. et al. Optimised nanoformulation of bromocriptine for direct nose-to-brain delivery: biodistribution, pharmacokinetic and dopamine estimation by ultra-HPLC/mass spectrometry method. Expert Opin. Drug Deliv. 11, 827-842 (2014).
33. Khan, M. S., Patil, K., Yeole, P. & Gaikwad, R. Brain targeting studies on buspirone hydrochloride after intranasal administration of mucoadhesive formulation in rats. J. Pharm. Pharmacol. 61, 669-675 (2009).
34. Barakat, N. S., Omar, S. A. & Ahmed, A. a. E. Carbamazepine uptake into rat brain following intra-olfactory transport. J. Pharm. Pharmacol. 58, 63-72 (2006).
35. Serralheiro, A., Alves, G., Fortuna, A. & Falcao, A. Intranasal administration of carbamazepine to mice: A direct delivery pathway for brain targeting. Eur. J. Pharm. Sci. 60, 32-39 (2014).
36. Wang, S., Chen, P., Zhang, L., Yang, C. & Zhai, G. Formulation and evaluation of microemulsion-based in situ ion-sensitive gelling systems for intranasal administration of curcumin. J. Drug Target. 20, 831-840 (2012).
37. Bhavna et al. Donepezil nanosuspension intended for nose to brain targeting: In vitro and in vivo safety evaluation. Int. J. Biol. Macromol. 67, 418-425 (2014).
38. Naik, A. & Nair, H. Formulation and Evaluation of Thermosensitive Biogels for Nose to Brain Delivery of Doxepin. BioMed Res. Int. 2014, e847547 (2014).
39. Alam, M. I. et al. Pharmacoscintigraphic evaluation of potential of lipid nanocarriers for nose-to-brain delivery of antidepressant drug. Int. J. Pharm. 470, 99-106 (2014).
40. Wang, X., He, H., Leng, W. & Tang, X. Evaluation of brain-targeting for the nasal delivery of estradiol by the microdialysis method. Int. J. Pharm. 317, 40-46 (2006).
41. Hanson, L. R. et al. Intranasal delivery of growth differentiation factor 5 to the central nervous system. Drug Deliv. 19, 149-154 (2012).
42. Shingaki, T. et al. Transnasal Delivery of Methotrexate to Brain Tumors in Rats: A New Strategy for Brain Tumor Chemotherapy. Mol. Pharm. 7, 1561-1568 (2010).
43. Wang, F., Jiang, X. & Lu, W. Profiles of methotrexate in blood and CSF following intranasal and intravenous administration to rats. Int. J. Pharm. 263, 1-7 (2003).
44. Westin, U. E., Bostrom, E., Grasjo, J., Hammarlund-Udenaes, M. & Bjork, E. Direct Nose-to-Brain Transfer of Morphine After Nasal Administration to Rats. Pharm. Res. 23, 565-572 (2006).
45. Zhang, Q. et al. Preparation of nimodipine-loaded microemulsion for intranasal delivery and evaluation on the targeting efficiency to the brain. Int. J. Pharm. 275, 85-96 (2004).
46. Abdelbary, G. A. & Tadros, M. I. Brain targeting of olanzapine via intranasal delivery of core—shell difunctional block copolymer mixed nanomicellar carriers: In vitro characterization, ex vivo estimation of nasal toxicity and in vivo biodistribution studies. Int. J. Pharm. 452, 300-310 (2013).
47. Seju, U., Kumar, A. & Sawant, K. K. Development and evaluation of olanzapine-loaded PLGA nanoparticles for nose-to-brain delivery: In vitro and in vivo studies. Acta Biomater. 7, 4169-4176 (2011).
48. Kumar, M., Misra, A., Mishra, A. K., Mishra, P. & Pathak, K. Mucoadhesive nanoemulsion-based intranasal drug delivery system of olanzapine for brain targeting. J. Drug Target. 16, 806-814 (2008).
49. Patel, M. R., Patel, R. B., Bhatt, K. K., Patel, B. G. & Gaikwad, R. V. Paliperidone microemulsion for nose-to-brain targeted drug delivery system: pharmacodynamic and pharmacokinetic evaluation. Drug Deliv. 1-9 (2014). doi:10.3109/10717544.2014.914602
50. Wang, D., Gao, Y. & Yun, L. Study on brain targeting of raltitrexed following intranasal administration in rats. Cancer Chemother. Pharmacol. 57, 97-104 (2006).
51. Ravi, P. R., Aditya, N., Patil, S. & Cherian, L. Nasal in-situ gels for delivery of rasagiline mesylate: improvement in bioavailability and brain localization. Drug Deliv. 1-8 (2013). doi:10.3109/10717544.2013.860501
52. Stevens, J., Ploeger, B. A., Graaf, P. H. van der, Danhof, M. & Lange, E. C. M. de. Systemic and Direct Nose-to-Brain Transport Pharmacokinetic Model for Remoxipride after Intravenous and Intranasal Administration. Drug Metab. Dispos. 39, 2275-2282 (2011).
53. Kumar, M. et al. Intranasal nanoemulsion based brain targeting drug delivery system of risperidone. Int. J. Pharm. 358, 285-291 (2008).
54. Patel, S. et al. Brain targeting of risperidone-loaded solid lipid nanoparticles by intranasal route. J. Drug Target. 19, 468-474 (2011).
55. Khan, S., Patil, K., Bobade, N., Yeole, P. & Gaikwad, R. Formulation of intranasal mucoadhesive temperature-mediated in situ gel containing ropinirole and evaluation of brain targeting efficiency in rats. J. Drug Target. 18, 223-234 (2010).
56. Mahajan, H. S., Mahajan, M. S., Nerkar, P. P. & Agrawal, A. Nanoemulsion-based intranasal drug delivery system of saquinavir mesylate for brain targeting. Drug Deliv. 21, 148-154 (2013).
57. Jogani, V. V., Shah, P. J., Mishra, P., Mishra, A. K. & Misra, A. R. Nose-to-brain delivery of tacrine. J. Pharm. Pharmacol. 59, 1199-1205 (2007).
58. Jogani, V. V. Mp., Shah, P. J. Mp., Mishra, P., Mishra, A. K. & Misra, A. R. P. *. Intranasal Mucoadhesive Microemulsion of Tacrine to Improve Brain Targeting. Alzheimer Dis. Assoc. Disord. April. 2008 22, 116-124 (2008).
59. Banks, W. A., Morley, J. E., Niehoff, M. L. & Mattern, C. Delivery of testosterone to the brain by intranasal administration: Comparison to intravenous testosterone. J. Drug Target. 17, 91-97 (2009).
60. Dahlin, M. & Bjork, E. Nasal absorption of (S)-UH-301 and its transport into the cerebrospinal fluid of rats. Int. J. Pharm. 195, 197-205 (2000).
61. Dalpiaz, A. et al. Brain Uptake of a Zidovudine Prodrug after Nasal Administration of Solid Lipid Microparticles. Mol. Pharm. 11, 1550-1561 (2014).
62. Jain, R., Nabar, S., Dandekar, P. & Patravale, V. Micellar Nanocarriers: Potential Nose-to-Brain Delivery of Zolmitriptan as Novel Migraine Therapy. Pharm. Res. 27, 655-664 (2010).
63. Brenneman, K. A. et al. Direct Olfactory Transport of Inhaled Manganese (54MnCl2) to the Rat Brain: Toxicokinetic Investigations in a Unilateral Nasal Occlusion Model. Toxicol. Appl. Pharmacol. 169, 238-248 (2000).
64. Henriksson, J., Tallkvist, J. & Tjalve, H. Transport of Manganese via the Olfactory Pathway in Rats: Dosage Dependency of the Uptake and Subcellular Distribution of the Metal in the Olfactory Epithelium and the Brain. Toxicol. Appl. Pharmacol. 156, 119-128 (1999).
65. Persson, E., Henriksson, J. & Tjalve, H. Uptake of cobalt from the nasal mucosa into the brain via olfactory pathways in rats. Toxicol. Lett. 145, 19-27 (2003).
66. Wolf, D. A. et al. Lysosomal enzyme can bypass the blood-brain barrier and reach the CNS following intranasal administration. Mol. Genet. Metab. 106, 131-134 (2012).
67. Thorne, R. G., Pronk, G. J., Padmanabhan, V. & Frey II, W. H. Delivery of insulin-like growth factor-I to the rat brain and spinal cord along olfactory and trigeminal pathways following intranasal administration. Neuroscience 127, 481-496 (2004).

68. Pardridge, W. M. Drug transport across the blood-brain barrier. J. Cereb. Blood Flow Metab. 32, 1959-1972 (2012).
69. Kandimalla, K. K. & Donovan, M. D. Transport of hydroxyzine and triprolidine across bovine olfactory mucosa: Role of passive diffusion in the direct nose-to-brain uptake of small molecules. Int. J. Pharm. 302, 133-144 (2005).
70. Dahlin, M., Jansson, B. & Bjork, E. Levels of dopamine in blood and brain following nasal administration to rats. Eur. J. Pharm. Sci. 14, 75-80 (2001).
71. Mistry, A., Stolnik, S. & Illum, L. Nanoparticles for direct nose-to-brain delivery of drugs. Int. J. Pharm. 379, 146-157 (2009).
72. Han, I.-K. et al. Enhanced brain targeting efficiency of intranasally administered plasmid DNA: an alternative route for brain gene therapy. J. Mol. Med. 85, 75-83 (2007).
73. Pietrowsky, R., Struben, C., Wile, M., Fehm, H. L. & Born, J. Brain potential changes after intranasal vs. intravenous administration of vasopressin: evidence for a direct nose-brain pathway for peptide effects in humans. Biol. Psychiatry 39, 332-340 (1996).
74. Fehm, H. L. et al. The Melanocortin Melanocyte-Stimulating Hormone/Adrenocorticotropin4-10 Decreases Body Fat in Humans. J. Clin. Endocrinol. Metab. 86, 1144-1148 (2001).
75. Danielyan, L. et al. Therapeutic Efficacy of Intranasally Delivered Mesenchymal Stem Cells in a Rat Model of Parkinson Disease. Rejuvenation Res. 14, 3-16 (2011).
76. Touitou, E. & Illum, L. Nasal drug delivery. Drug Deliv. Transl. Res. 3, 1-3 (2013).
77. Nakamura, F., Ohta, R., Machida, Y. & Nagai, T. In vitro and in vivo nasal mucoadhesion of some water-soluble polymers. Int. J. Pharm. 134, 173-181 (1996).
78. Pennington, A. K., Ratcliffe, J. H., Wilson, C. G. & Hardy, J. G. The influence of solution viscosity on nasal spray deposition and clearance. Int. J. Pharm. 43, 221-224 (1988).
79. Charlton, S., Jones, N. S., Davis, S. S. & Illum, L. Distribution and clearance of bioadhesive formulations from the olfactory region in man: Effect of polymer type and nasal delivery device. Eur. J. Pharm. Sci. 30, 295-302 (2007).
80. Chaturvedi, M., Kumar, M. & Pathak, K. A review on mucoadhesive polymer used in nasal drug delivery system. J. Adv. Pharm. Technol. Res. 2, 215-222 (2011).
81. Jose, S. et al. Thermo-sensitive gels containing lorazepam microspheres for intranasal brain targeting. Int. J. Pharm. 441, 516-526 (2013).
82. Cai, Z. et al. Formulation and Evaluation of In Situ Gelling Systems for Intranasal Administration of Gastrodin. AAPS PharmSciTech 12, 1102-1109 (2011).
83. Gao, X. et al. Lectin-conjugated PEG-PLA nanoparticles: Preparation and brain delivery after intranasal administration. Biomaterials 27, 3482-3490 (2006).
84. Gao, X. et al. Brain delivery of vasoactive intestinal peptide enhanced with the nanoparticles conjugated with wheat germ agglutinin following intranasal administration. J. Controlled Release 121, 156-167 (2007).
85. Liu, Q. et al. In vivo toxicity and immunogenicity of wheat germ agglutinin conjugated poly(ethylene glycol)-poly(lactic acid) nanoparticles for intranasal delivery to the brain. Toxicol. Appl. Pharmacol. 251, 79-84 (2011).
86. Sharma, D. et al. Formulation and Optimization of Polymeric Nanoparticles for Intranasal Delivery of Lorazepam Using Box-Behnken Design: In Vitro and In Vivo Evaluation. BioMed Res. Int. 2014, e156010 (2014).
87. Fazil, M. et al. Development and evaluation of rivastigmine loaded chitosan nanoparticles for brain targeting. Eur. J. Pharm. Sci. 47, 6-15 (2012).
88. Dhuria, S. V., Hanson, L. R. & Frey, W. H. Novel vasoconstrictor formulation to enhance intranasal targeting of neuropeptide therapeutics to the central nervous system. J. Pharmacol. Exp. Ther. 328, 312-320 (2009).
89. Drejer, K. et al. Intranasal Administration of Insulin With Phospholipid as Absorption Enhancer: Pharmacokinetics in Normal Subjects. Diabet. Med. 9, 335-340 (1992).
90. Gordon, G. S., Moses, A. C., Silver, R. D., Flier, J. S. & Carey, M. C. Nasal absorption of insulin: enhancement by hydrophobic bile salts. Proc. Natl. Acad. Sci. 82, 7419-7423 (1985).
91. Behl, C. R. et al. Optimization of systemic nasal drug delivery with pharmaceutical excipients. Adv. Drug Deliv. Rev. 29, 117-133 (1998).
92. Arora, P., Sharma, S. & Garg, S. Permeability issues in nasal drug delivery. Drug Discov. Today 7, 967-975 (2002).
93. Karasulu, E., Yavaoglu, A., Evrenpnal, Z., Uyamkgil, Y. & Karasulu, H. Y. Permeation Studies and Histological Examination of Sheep Nasal Mucosa Following Administration of Different Nasal Formulations with or without Absorption Enhancers. Drug Deliv. 15, 219-225 (2008).
94. Karasulu, H. Y., Sanal, Z. E., Sozer, S., Gtmeri, T. & Ertan, G. Permeation Studies of Indomethacin from Different Emulsions for Nasal Delivery and Their Possible Anti-Inflammatory Effects. AAPS PharmSciTech 9, 342-348 (2008).
95. Lu, Y. et al. Bioavailability and Brain-Targeting of Geniposide in Gardenia-Borneol Co-Compound by Different Administration Routes in Mice. Int. J. Mol. Sci. 13, 14127-14135 (2012).
96. Jadhav, K. R., Shaikh, I. M., Ambade, K. W. & Kadam, V. J. Applications of Microemulsion Based Drug Delivery System. Curr. Drug Deliv. 3, 267-273 (2006).
97. Shah, B. M., Misra, M., Shishoo, C. J. & Padh, H. Nose to brain microemulsion-based drug delivery system of rivastigmine: formulation and ex-vivo characterization. Drug Deliv. 1-13 (2014). doi:10.3109/10717544.2013.878857
98. Hosny, K. M. & Hassan, A. H. Intranasal in situ gel loaded with saquinavir mesylate nanosized microemulsion: Preparation, characterization, and in vivo evaluation. Int. J. Pharm. 475, 191-197 (2014).
99. Sood, S., Jain, K. & Gowthamarajan, K. Optimization of curcumin nanoemulsion for intranasal delivery using design of experiment and its toxicity assessment. Colloids Surf. B Biointerfaces 113, 330-337 (2014).
100. Montenegro, L. et al. In vitro evaluation of idebenone-loaded solid lipid nanoparticles for drug delivery to the brain. Drug Dev. Ind. Pharm. 37, 737-746 (2011).
101. Pardeshi, C. V., Rajput, P. V., Belgamwar, V. S., Tekade, A. R. & Surana, S. J. Novel surface modified solid lipid nanoparticles as intranasal carriers for ropinirole hydrochloride: application of factorial design approach. Drug Deliv. 20, 47-56 (2013).
102. Behl, C. R.; Pimplaskar, H. K.; Sileno, A. P.; deMeireles, J.; Romeo, V. D. Effects of physicochemical properties and other factors on systemic nasal drug delivery. Advanced Drug Delivery Reviews 1998, 29, (1-2), 89-116.

103. Newman, S. P.; Pitcairn, G. R.; Dalby, R. N. Drug delivery to the nasal cavity: in vitro and in vivo assessment. Critical Reviews™ in Therapeutic Drug Carrier Systems 2004, 21, (1).

104. Warnken, Z.; Smyth, H. D.; Williams III, R. O., Route-Specific Challenges in the Delivery of Poorly Water-Soluble Drugs. In Formulating Poorly Water Soluble Drugs, Springer: 2016; pp 1-39.

105. Hoekman, J. D.; Ho, R. J. Y. Enhanced Analgesic Responses After Preferential Delivery of Morphine and Fentanyl to the Olfactory Epithelium in Rats. Anesthesia & Analgesia 2011, 1.

106. Warnken, Z. N.; Smyth, H. D. C.; Watts, A. B.; Weitman, S.; Kuhn, J. G.; Williams Iii, R. Formulation and device design to increase nose to brain drug delivery. Journal of Drug Delivery Science and Technology 2016, 35, 213-222.

107. Illum, L. Nasal drug delivery—possibilities, problems and solutions. Journal of Controlled Release 2003, 87, 187-198.

108. Djupesland, P. G. Nasal drug delivery devices: characteristics and performance in a clinical perspective—a review. Drug Delivery and Translational Research 2013, 3, 42-62.

109. Cheng, Y.; Yeh, H.; Guilmette, R.; Simpson, S.; Cheng, K.; Swift, D. Nasal deposition of ultrafine particles in human volunteers and its relationship to airway geometry. Aerosol Science and Technology 1996, 25, (3), 274-291.

110. Kundoor, V.; Dalby, R. N. Effect of formulation- and administration-related variables on deposition pattern of nasal spray pumps evaluated using a nasal cast. Pharmaceutical Research 2011, 28, (8), 1895-1904.

111. Foo, M. Y.; Cheng, Y. S.; Su, W. C.; Donovan, M. D. The influence of spray properties on intranasal deposition. Journal of aerosol medicine: the official journal of the International Society for Aerosols in Medicine 2007, 20, (4), 495-508.

112. Doughty, D. V.; Hsu, W.; Dalby, R. N. Automated actuation of nasal spray products: effect of hand-related variability on the in vitro performance of Flonase nasal spray. Drug Dev Ind Pharm 2014, 40, (6), 711-8.

113. Guo, C.; Stine, K. J.; Kauffman, J. F.; Doub, W. H. Assessment of the influence factors on in vitro testing of nasal sprays using Box-Behnken experimental design. European Journal of Pharmaceutical Sciences 2008, 35, (5), 417-426.

114. Cheng, Y.; Holmes, T.; Gao, J.; Guilmette, R.; Li, S.; Surakitbanharn, Y.; Rowlings, C. Characterization of nasal spray pumps and deposition pattern in a replica of the human nasal airway. Journal of Aerosol Medicine 2001, 14, (2), 267-280.

115. Guo, Y.; Laube, B.; Dalby, R. The effect of formulation variables and breathing patterns on the site of nasal deposition in an anatomically correct model. Pharm Res 2005, 22, (11), 1871-8.

116. Swift, D. Inspiratory inertial deposition of aerosols in human nasal airway replicate casts: implication for the proposed NCRP lung model. Radiation Protection Dosimetry 1991, 38, (1-3), 29-34.

117. Samolifiski, B. K.; Grzanka, A.; Gotlib, T. Changes in Nasal Cavity Dimensions in Children and Adults by Gender and Age. The Laryngoscope 2007, 117, (8), 1429-1433.

118. Hsu, D.-J.; Chuang, M.-H. In-Vivo Measurements of Micrometer-Sized Particle Deposition in the Nasal Cavities of Taiwanese Adults. Aerosol Science and Technology 2012, 46, (6), 631-638.

119. Liu, Y.; Johnson, M. R.; Matida, E. A.; Kherani, S.; Marsan, J. Creation of a standardized geometry of the human nasal cavity. Journal of Applied Physiology 2009, 106, (3), 784-795.

120. Fedorov, A.; Beichel, R.; Kalpathy-Cramer, J.; Finet, J.; Fillion-Robin, J.-C.; Pujol, S.; Bauer, C.; Jennings, D.; Fennessy, F.; Sonka, M.; Buatti, J.; Aylward, S.; Miller, J. V.; Pieper, S.; Kikinis, R. 3D Slicer as an Image Computing Platform for the Quantitative Imaging Network. Magnetic resonance imaging 2012, 30, (9), 1323-1341.

121. Doughty, D. V.; Vibbert, C.; Kewalramani, A.; Bollinger, M. E.; Dalby, R. N. Automated actuation of nasal spray products: determination and comparison of adult and pediatric settings. Drug Development and Industrial Pharmacy 2011, 37, (3), 359-366.

122. Schindelin, J.; Arganda-Carreras, I.; Frise, E.; Kaynig, V.; Longair, M.; Pietzsch, T.; Preibisch, S.; Rueden, C.; Saalfeld, S.; Schmid, B. Fiji: an open-source platform for biological-image analysis. Nature methods 2012, 9, (7), 676-682.

123. Zhou, Y.; Guo, M.; Xi, J.; Irshad, H.; Cheng, Y.-S. Nasal deposition in infants and children. Journal of aerosol medicine and pulmonary drug delivery 2014, 27, (2), 110-116.

124. Garcia, G. J.; Tewksbury, E. W.; Wong, B. A.; Kimbell, J. S. Interindividual variability in nasal filtration as a function of nasal cavity geometry. Journal of aerosol medicine and pulmonary drug delivery 2009, 22, (2), 139-156.

125. D., S. Inspiratory inertial deposition of aerosols in human nasal airway replicate casts: Implication for the proposed NCRP lung model. Radiation Protection Dosimetry 1991, 38, (1/3), 29-34.

126. Sadee, W. Personalized Therapeutics and Pharmacogenomics: Integral to Personalized Health Care. Pharmaceutical Research 2017, 34, (8), 1535-1538.

127. Inthavong, K.; Fung, M. C.; Yang, W.; Tu, J. Measurements of droplet size distribution and analysis of nasal spray atomization from different actuation pressure. Journal of aerosol medicine and pulmonary drug delivery 2015, 28, (1), 59-67.

128. Pu, Y.; Goodey, A. P.; Fang, X.; Jacob, K. A Comparison of the Deposition Patterns of Different Nasal Spray Formulations Using a Nasal Cast. Aerosol Science and Technology 2014, 48, (9), 930-938.

129. Kimbell, J. S.; Segal, R. A.; Asgharian, B.; Wong, B. A.; Schroeter, J. D.; Southall, J. P.; Dickens, C. J.; Brace, G.; Miller, F. J. Characterization of Deposition from Nasal Spray Devices Using A Computational Fluid Dynamics Model of The Human Nasal Passages. Journal of Aerosol Medicine 2007, 20, (1), 59-74.

130. Xi, J.; Yuan, J. E.; Zhang, Y.; Nevorski, D.; Wang, Z.; Zhou, Y. Visualization and Quantification of Nasal and Olfactory Deposition in a Sectional Adult Nasal Airway Cast. Pharmaceutical Research 2016, 33, (6), 1527-1541.

131. Aggarwal, R.; Cardozo, A.; Homer, J. J. The assessment of topical nasal drug distribution. Clinical Otolaryngology & Allied Sciences 2004, 29, (3), 201-205.

132. Kelly, J. T.; Asgharian, B.; Kimbell, J. S.; Wong, B. A. Particle Deposition in Human Nasal Airway Replicas Manufactured by Different Methods. Part I: Inertial Regime Particles. Aerosol Science and Technology 2004, 38, 1063-1071.

133. Kelly, J. T.; Asgharian, B.; Kimbell, J. S.; Wong, B. A. Particle deposition in human nasal airway replicas manufactured by different methods. Part I: Inertial regime particles. Aerosol Science and Technology 2004, 38, (11), 1063-1071.
134. Schroeter, J. D.; Garcia, G. J.; Kimbell, J. S. Effects of surface smoothness on inertial particle deposition in human nasal models. Journal of aerosol science 2011, 42, (1), 52-63.

The invention claimed is:

1. An apparatus for nasal administration of a pharmaceutical composition, the apparatus comprising:
   a reservoir;
   a conduit in fluid communication with the reservoir;
   an actuator configured to transfer a pharmaceutical composition from the reservoir to the conduit and emit the pharmaceutical composition from the conduit; and
   an anatomic positioning device configured to position the conduit in a nasal cavity of a user, wherein:
   the anatomic positioning device is configured to emit the pharmaceutical composition from the conduit at a sagittal angle between about 50.3 and 67.1 degrees; and
   the anatomic positioning device is configured to emit the pharmaceutical composition from the conduit at a coronal angle between about -3.8 and 23.1 degrees.

2. The apparatus of claim 1 wherein the conduit is threaded and the adjustable member is threadably coupled to the conduit.

3. The apparatus of claim 1 wherein the anatomic positioning device further comprises:
   a dial mechanism for controlling the depth and the angle at which the conduit is inserted into the nasal cavity.

4. The apparatus of claim 1 wherein further comprising a sensor configured to detect an angle at which the conduit is positioned.

5. The apparatus of claim 4 wherein the sensor is a mechanical sensor.

6. The apparatus of claim 4 wherein the sensor is an electronic sensor.

* * * * *